(12) United States Patent
Lízio et al.

(10) Patent No.: US 8,734,849 B2
(45) Date of Patent: *May 27, 2014

(54) MULTIPARTICLE PHARMACEUTICAL DOSAGE FORM CONTAINING A MUCOADHESIVELY FORMULATED PEPTIDE OR PROTEIN ACTIVE SUBSTANCES METHOD FOR PRODUCING SAID PHARMACEUTICAL DOSAGE FORM

(75) Inventors: Rosario Lízio, Rossdorf (DE); Hans-Ulrich Petereit, Darmstadt (DE); Erna Roth, Darmstadt (DE); Inès Andres, Varese (IT); Michael Damm, Rödermark (DE)

(73) Assignee: Evonik Roehm GmbH, Darmstadt (DE)

( * ) Notice: Subject to any disclaimer, the term of this patent is extended or adjusted under 35 U.S.C. 154(b) by 846 days.

This patent is subject to a terminal disclaimer.

(21) Appl. No.: 10/564,096

(22) PCT Filed: Jul. 15, 2004

(86) PCT No.: PCT/EP2004/007882
§ 371 (c)(1),
(2), (4) Date: May 2, 2006

(87) PCT Pub. No.: WO2005/007139
PCT Pub. Date: Jan. 27, 2005

(65) Prior Publication Data
US 2007/0026082 A1    Feb. 1, 2007

(30) Foreign Application Priority Data
Jul. 15, 2003   (DE) .................................... 103 32 160

(51) Int. Cl.
*A61K 9/14*    (2006.01)

(52) U.S. Cl.
USPC ............................ 424/490; 424/493; 424/501

(58) Field of Classification Search
None
See application file for complete search history.

(56) References Cited

U.S. PATENT DOCUMENTS 5,849,327 A * 12/1998 Berliner et al. ............... 424/463
6,465,626 B1 * 10/2002 Watts et al. ..................... 536/20
6,468,959 B1   10/2002 Wunderlich et al.

FOREIGN PATENT DOCUMENTS

| DE | 100 24 451 | 11/2001 |
| EP | 1 203 590 | 5/2002 |
| JP | 5-132416 | 5/1993 |
| JP | 11-116499 A | 4/1999 |
| WO | 93/13753 | 7/1993 |
| WO | 95/18602 | 7/1995 |
| WO | WO 01/43728 A1 | 6/2001 |
| WO | 02/03955 | 1/2002 |
| WO | WO 02/11694 A2 | 2/2002 |
| WO | 02/43767 | 6/2002 |
| WO | 02/064148 | 8/2002 |
| WO | 03/007913 | 1/2003 |

OTHER PUBLICATIONS

Mucin entry from Stedman's Chemical Dictionary, 2000.*
Mucus entry from Stedman's Chemical Dictionary, 2000.*
Glycocalyx entry from Stedman's Chemical Dictionary, 2000.*
Lorenzo-Lamosa et al. J Controlled Release 52, p. 109-118, 1998.*
Thanou et al. Adv Drug Delivery Reviews 50, p. S91-S101, 2001.*
Definitin of "embed" from thefreedictionary.com, accessed Oct. 10, 2012.*
Trenktrog et al. "Enteric coated insulin pellets: development, drug release and in vivo evaluation", European Journal of Pharmaceutical Sciences, vol. 4, pp. 323-329 1996.
Takeuchi et al. "Enteral Absorption of Insulin in Rats from Mucoadhesive Chitosan-Coated Liposomes", Pharmaceutical Research, vol. 13, No. 6, pp. 896-901 1996.
Dorkoosh et al. "Peroral drug delivery systems for peptides and proteins", S.T.P. Pharma Sciences, vol. 12, No. 4, pp. 213-221 2002.
Bernkop-Schnuerch. "The use of multifunctional polymers for non-invasive peptide and protein application", Exp. Opin. Ther. Patents, vol. 10, No. 9, pp. 1357-1366 2000.
U.S. Appl. No. 10/572,963, filed Mar. 21, 2006, Lizio, et al.
U.S. Appl. No. 10/573,019, filed Mar. 22, 2006, Lizio, et al.
U.S. Appl. No. 11/569,581, filed Nov. 24, 2006, Dressman, et al.
Office Action issued Apr. 26, 2011, in Canadian Patent Application No. 2,532,487.

* cited by examiner

*Primary Examiner* — Nissa Westerberg
(74) *Attorney, Agent, or Firm* — Oblon, Spivak, McClelland, Maier & Neustadt, L.L.P.

(57) ABSTRACT

The invention relates to an oral, multiparticle pharmaceutical dosage form containing pellets, the size of which ranges from 50 to 2500 μm and which essentially consist of: a) an inner matrix layer containing an active substance which is a peptide or a protein, including the derivatives or conjugates thereof, and which is embedded in a matrix consisting of a polymer with mucoadhesive effect, and b) an outer film coating essentially consisting of an anionic polymer or copolymer, which can be optionally formulated with pharmaceutically conventional adjuvants, more particularly softening agents.

20 Claims, No Drawings

MULTIPARTICLE PHARMACEUTICAL DOSAGE FORM CONTAINING A MUCOADHESIVELY FORMULATED PEPTIDE OR PROTEIN ACTIVE SUBSTANCES METHOD FOR PRODUCING SAID PHARMACEUTICAL DOSAGE FORM

The invention relates to a multiparticulate pharmaceutical form comprising mucoadhesively formulated peptide and/or protein active substances, and to a method for producing the pharmaceutical form.

PRIOR ART

DE 100 24 451 A1 describes pharmaceutical dosage forms suitable for parenteral use and comprising, in dissolved or dispersed form, peptides which are prone to aggregation. The peptides may in this case be present in various salt forms. The dosage forms comprise in addition free acids and, where appropriate, further pharmaceutical excipients.

WO 02/03955 describes bioadhesive, microspherically formulated pharmaceutical forms for sublingual administration of active substances. The microspheres have an average diameter of less than 50 μm and comprise the active substance, which may be for example a peptide, in non-crystalline form in a micromatrix embedded in a bioadhesive polymer. The bioadhesive polymer may be inter alia a cellulose, a chitosan or an acrylic copolymer.

WO 02/64148 describes formulations comprising a mucopolysaccharide and a method for their production. In this case a mucopolysaccharide, e.g. heparin, is formulated together with an adsorption enhancer, e.g. a chitosan, and then provided with a coating soluble in intestinal juice, so that the active substance can be released in the middle or lower segments of the small intestine. Examples of suitable coatings soluble in intestinal juice are anionic acrylic copolymers of the type of Eudragit® L, S, L100-55. The formulations may include capsules, tablets and granules.

WO 02/43767 describes oral pharmaceutical compositions for physiologically active peptide active substances comprising the active substance, which is coupled to a cell membrane translocator, a pH-lowering agent and/or a protease inhibitor and an acid-stable transport vehicle which protects the pharmaceutical composition when passing through the patient's stomach and prevents contact with the proteases present in the stomach. The transport vehicle may be capsules which are coated with acid-resistant coatings composed of Eudragit® L30 D-55.

WO 03/007913 describes oral multiparticulate pharmaceutical forms which comprise the active substance in the form of a multiplicity of so-called patches. A patch is a discus-shaped object made of biocompatible material having a diameter of from 500 μm to 5 mm and a height of from 100 to 1000 μm. The patch consists of two layers or sides, of one side which has only low permeability for water or body fluids, e.g. made of ethylcellulose, and of a second side which comprises the active substance, e.g. a peptide or protein, which may be present in a mixture with mucoadhesive polymers, e.g. chitosan, CMC, polyacrylic acid or pectin. The patches can be compressed to form a tablet or else be packed into a capsule which is additionally provided with a coating soluble in intestinal juice. The active substance preparations may also be combined additionally with so-called enhancers such as fatty acids, fatty alcohols, esters, surface-active substances and protease inhibitors. At the site of action, e.g. in a particular segment of the intestine, the capsule dissolves and releases the patches. The released patches are able to adhere with their mucoadhesive side to the intestinal mucosa and there deliver the active substance in a delayed manner and directly toward the intestinal mucosa. The second, only slightly permeable side of the patches is intended to provide the active substance with a certain protection against chemical or enzymatic inactivation from the side facing the intestinal lumen and also to prevent the active substance escaping on this side.

Problem and Solution

The solution offered by WO 03/007913 to the production of oral pharmaceutical forms, especially for peptide- or protein-based active substances which are released in the intestinal lumen and are intended to act there, is notable and is to be acknowledged. One disadvantage of this solution is inter alia the elaborate construction and production of the two-layer patch structures. It appears particularly unfavorable, however, for the pharmaceutical form to be provided as capsule having a coating which is resistant to gastric juice and soluble in intestinal juice. The size of distinctly more than 2.5 mm results in this case in an inadequate therapeutic reproducibility. The time for the capsule to pass through the stomach may vary widely. In any event, a delayed onset of action is to be expected. In addition, the capsule may itself dissolve rapidly or slowly after partial dissolution of the coating. The two principles of coating and capsule overlap in an unfavorable way in this case, so that the release of the patches must be expected overall to be uncontrolled. The capsule may, in a situation where it is at least partly accessible to the intestinal juices, remain intact or else be substantially broken down mechanically, depending on the current intestinal contents or intestinal peristalsis. There may be on the one hand a sudden release of large amounts of patches, or on the other hand also an unwanted delay of release, depending on the disintegration or mechanical stress on the initially coated capsule structure. An active substance delivery which can overall be controlled better would therefore be desirable.

It has been regarded as one of the problems of the invention to provide a pharmaceutical form which is suitable for the targeted and efficient release of protein or peptide active substances. The pharmaceutical form is intended to provide high dosage reliability and be distributed well in the intestinal lumen after a rapid passage through the stomach. The contained protein or peptide active substance is moreover intended to be protected substantially from physical, chemical or proteolytic inactivation and to be released at the defined site of action in such a way that a large proportion of the active substance can be absorbed by the body. The site of release is intended to be variably and reliably adjustable depending on the therapeutic aim.

The problem is solved by an
oral multiparticulate pharmaceutical form comprising pellets having a size in the range from 50 to 2500 μm, which are composed of
  a) an inner matrix layer comprising an active substance which is a peptide or a protein, including derivatives or conjugates thereof, and is embedded in a matrix of a polymer having a mucoadhesive effect, where the matrix may optionally comprise further pharmaceutically usual excipients,
  b) an outer film coating consisting essentially of an anionic polymer or copolymer which may optionally be formulated with pharmaceutically usual excipients, especially plasticizers,
characterized in that
the multiparticulate pharmaceutical form is formulated so that the contained pellets are released in the pH range of the stomach, the outer coating is adjusted through the choice of the anionic polymer or copolymer or its formulation with excipients and its layer thickness such that the coating dissolves in pH ranges from 4.0 to 8.0 in the intestine within 15 to 60 min, so that the active substance-containing, mucoadhesive matrix layer is exposed, and can bind to the intestinal mucosa and release the active substance there, where the polymer having a mucoadhesive effect is chosen so that it exhibits a mucoadhesive effect of at least $\eta_b$=150 to 1000 mPa·s and a water uptake of from 10 to 750% in 15 min in a range of +/−0.5 pH units relative to the pH at which the outer coating starts to dissolve, and the active substance content of the matrix layer is a maximum of 40% by weight of the content of polymer having a mucoadhesive effect.

Implementation of the Invention

The invention relates to an oral multiparticulate pharmaceutical form, in particular in the form of a tablet, minitablet, pellets packed into capsules or sachets or reconstitutable powders, comprising pellets having an average size or average diameter in the range from 50 to 2500, preferably from 100 to 1000, μm, which are composed of a) an inner matrix layer comprising an active substance which is a peptide or a protein, including derivatives or conjugates thereof, and is embedded in a matrix of a polymer having a mucoadhesive effect, where the matrix may optionally or ordinarily comprise further pharmaceutically usual excipients, b) an outer film coating consisting essentially of an anionic polymer or copolymer which may optionally be formulated with pharmaceutically usual excipients, especially plasticizers, The multiparticulate pharmaceutical form is formulated so that the contained pellets are released in the pH range of the stomach.

The outer coating is adjusted through the choice of the anionic polymer or copolymer or its formulation with excipients and its layer thickness such that the coating dissolves in pH ranges from 4.0 to 8.0, preferably from 5.5 to 7.8, particularly preferably 5.8 to 7.5, in the intestine within 15 to 60, preferably from 20 to 40, min so that the active substance-containing, mucoadhesive matrix layer is exposed, and can bind to the intestinal mucosa and release the active substance there.

The polymer or copolymer having a mucoadhesive effect is chosen so that it exhibits a mucoadhesive effect of at least $\eta_b$=150 to 1000, preferably 150 to 600, mPa·s and a water uptake of from 10 to 750, preferably 10 to 250, particularly preferably 10 to 160% in 15 min in a range of +/−0.5, preferably +/−0.3, pH units relative to the pH at which the outer coating starts to dissolve, and the active substance content of the matrix layer is a maximum of 40, in particular 0.001 to 15 or 0.05 to 5, % by weight of the content of polymer having a mucoadhesive effect.

The Inner Matrix Layer

The inner matrix layer acts as active substance carrier. The inner matrix layer additionally has the function of binding the active substance, by means of the contained mucoadhesive polymer, to the intestinal mucosa so that the active substance can enter the body therefrom. The inner matrix layer further has the function of protecting the active substance from physical, chemical or enzymatic inactivation.

Active Substances/Active Substance Formulations

The matrix layer comprises an active substance which may be a protein or peptide, including derivatives or conjugates thereof, having an average molecular weight $M_w$ of from 300 to 1 000 000 (daltons). By derivatives are meant chemical or biochemical modifications of the primary or secondary structure. Examples are proteins or peptides which are derived from natural sources or are completely synthetic and have non-natural amino acid residues. Conjugates are covalent linkages of proteins or peptides to non-peptidic compounds, e.g. proteins or peptides coupled to polyethylene glycol.

Active Substances

The active substances employed for the purposes of the invention are intended in particular to be used on or in the human or animal body in order 1. to cure, to alleviate, to prevent or to diagnose disorders, conditions, physical damage or pathological symptoms.
2. to reveal the condition, the status or the functions of the body or mental states.
3. to replace active substances or body fluids produced by the human or animal body.
4. to ward off, to eliminate or to render harmless pathogens, parasites or exogenous substances or
5. to influence the condition, the status or the functions of the body or mental states.

The peptide and protein active substances can be employed as free acids or bases. Examples of counter ions which can be employed are physiologically bases or acids, tolerated alkaline earth metals or alkali metals or amines and, for example, acetate, adipate, ascorbate, alginate, benzoate, benzenesulfonate, bromide, carbonate, carboxymethylcellulose (free acid), citrate, chloride, dibutyl phosphate, dihydrogen citrate, dioctyl phosphate, dihexadecyl phosphate, fumarate, gluconate, glucuronate, glutamate, hydrogen carbonate, hydrogen tartrate, hydrochloride, hydrogen citrate, iodide, lactate, alpha-lipoate, malate, maleate, malonate, pamoate, palmitate, phosphate, salicylate, stearate, succinate, sulfate, tartrate, tannates, oleate, octyl phosphate.

The active substance content of the matrix layer is a maximum of 40, in particular 0.001 to 15 or 0.05 to 5, % by weight of the content of polymer having a mucoadhesive effect.

Depending on the physicochemical properties of the active substance, such as, for example, water in oil partition coefficient or isoelectric point etc., the matrix layer may additionally comprise a $C_6$- to $C_{20}$-, preferably $C_8$-, $C_{10}$- or $C_{12}$- to $C_{20}$-carboxylic or fatty acid and/or a $C_6$- to $C_{20}$-, preferably $C_8$-, $C_{10}$- or $C_{10}$- to $C_{20}$-alcohol including their salts, ether, ester or amide derivatives and/or a lipid and/or a phospholipid and/or a lipid-soluble vitamin and/or a protease inhibitor and/or a penetration promoter and/or an efflux pump inhibitor, e.g. ketoconazole or polyethylene 660 12-hydroxystearate (Solutol® HS15).

The active substance may be a protein or a peptide having an average molecular weight $M_w$ of less than 3000 Da. Examples of such peptides are in particular abarelix, angiotensin II, anidulafungin, antide, argipressin, azaline and azaline B, bombesin antagonist, bradykinin, buserelin, cetrorelix, cyclosporine A, desmopressin, detirelix, encephalins (Leu-, Met-) ganirelix, gonadorelin, goserelin, growth hormone secretagogue, micafungin, nafarelin, leuprolide, leuprorelin, octreotide, orntide, oxytocin, ramorelix, secretin, somatotropin, terlipressin, tetracosactide, teverelix, triptorelin, thyroliberin, thyrotropin, vasopressin.

It is preferred in this case for the matrix layer additionally to comprise a $C_6$- to $C_{20}$-, preferably $C_8$-, $C_{10}$- or $C_{12}$- to $C_{20}$-, optionally up to $C_{30}$-carboxylic or fatty acid and/or a $C_6$- to $C_{20}$-, preferably $C_8$-, $C_{10}$- or $C_{12}$- to $C_{20}$-, optionally up to $C_{30}$-alcohol, including their salts, ether, ester or amide derivatives and/or a lipid and/or a phospholipid and/or a lipid-soluble vitamin and/or an efflux pump inhibitor. The addition has the advantage that the solubility, stability and uptake of the active substance may be improved thereby.

Suitable examples are esters of fatty acids such as glycerol trimyristate, glycerol monostearate, glycerol tristearate, glycerol tripalmitate, glyceryl behenic acid ester and fatty acid amides, aliphatic long-chain carboxylic acids such as palmitic acid, stearic acid, lauric acid, myristic acid, fatty alcohols such as stearyl alcohol, lauryl alcohol, cetyl alcohol, and waxes such as carnauba wax, beeswax, and phospholipids such as egg lecithin, soybean lecithin, and vitamins such as vitamin E.

The active substance may be a protein or peptide having an average molecular weight $M_w$ of from 3000 to 10 000 Da. Examples of such proteins or peptides are in particular calcitonin, corticotrophin, endorphins, epithelial growth factor, glucagon, insulin, novolin, parathyroid hormone, relaxin, pro-somatostatin, salmon secretin.

If the active substance is a protein or peptide having an average molecular weight $M_w$ of from 3000 to 10 000, the matrix layer preferably comprises a $C_6$- to $C_{20}$-, preferably $C_8$-, $C_{10}$- or $C_{12}$- to $C_{20}$-, where appropriate up to $C_{30}$-carboxylic or fatty acid and/or a $C_6$- to $C_{20}$-, preferably $C_8$-, $C_{10}$- or $C_{12}$- to $C_{20}$-, where appropriate up to $C_{30}$-alcohol, including their salts, ether, ester or amide derivatives and/or a lipid and/or a phospholipid and/or a lipid-soluble vitamin and/or a protease inhibitor.

Protein or peptide active substances having an average molecular weight $M_w$ of from 3000 to 10 000 are often particularly sensitive to enzymatic degradation by proteases, so that the addition of protease inhibitors is particularly advantageous per se, besides the stabilization of the active substance.

Examples of pharmaceutically suitable protease inhibitors are antipain, aprotinin, bacitracin, benzamidine, bestatin, captopril, chymostatin, chicken ovoinhibitor, EDTA $Na_2$, chitosan-EDTA conjugates, Na glycocholates, leupeptin, pepstatin, soybean trypsin inhibitors, thiorphan, tos-lys chloromethyl ketone, potato carboxypeptidase inhibitor.

The active substance may be a protein or peptide having an average molecular weight $M_w$ of more than 10 000. Examples of such proteins or peptides are in particular interferons (alpha, beta, gamma), interleukins (IL1, IL2), somatotropin, erythropoietin, tumor necrosis factor (TNF alpha, beta), relaxin, endorphin, domase alpha, follicle stimulating hormone (FSH), human chorion gonadotropin (HCG), human growth hormone release factor (hGRF), luteinizing hormone (LH) or epidermal growth factor.

If the active substance is a protein or peptide having an average molecular weight $M_w$ of more than 10 000 Da, the matrix layer preferably additionally comprises a $C_6$- to $C_{20}$-, preferably $C_8$-, $C_{10}$- or $C_{12}$- to $C_{20}$-, where appropriate up to $C_{30}$ carboxylic or fatty acid and/or a $C_6$- to $C_{20}$-, preferably $C_8$-, $C_{10}$- or $C_{12}$- to $C_{20}$-, where appropriate up to $C_{30}$ alcohol, including their salts, ether, ester or amide derivatives and/or a lipid and/or a phospholipid and/or a lipid-soluble vitamin and/or a protease inhibitor and/or a penetration promoter.

The addition of a penetration promoter is advantageous because uptake of the active substance having a comparatively high average molecular weight $M_w$ of more than 10 000 is favored thereby.

Suitable penetration promoters are in particular plasticizers such as, for example, triethyl citrate, acetyl triethyl citrate, diethyl sebacate, dibutyl sebacate, polymers such as carbomer, chitosan, chitosan-cysteine, sodium carboxymethylcellulose, N-trimethylated chitosan, polycarbophil-cysteines, long-chain fatty acids, their esters (for example mono and diglycerides) and their salts such as lauric acid, laurinsulfonic acid, palmitic acid, caprylic acid, capric acid, oleic acid, acylcarnitines, chelating agents such as EDTA, salicylates, cyclodextrins, polyacrylic acids, bile acids such as cholic acid, cholyltaurine, cholylsarcosine, chenodeoxycholic acid and their salts such as Na cholate, Na glycocholate, Na taurocholate, Na taurodihydrofusidate, Na glycodihydrofusidate, surfactants and emulsifiers such as, in particular, polyethylene 660 12-hydroxystearate (Solutol® HS15) (Solutol HS15), polysorbate 80 (Tween 80), polyethoxylated castor oil (Cremophor EL), polyoxyethylene-polyoxypropylene glycol (Pluronic® F68), the toxin zonula occludens toxin (ZOT) and vitamins such as vitamin E (tocopherol) or vitamin B12.

If the active substance is a protein or peptide having a high molecular weight $M_w$ of more than 10 000, the matrix layer preferably additionally comprises an efflux pump inhibitor such as, in particular, ketoconazole or polyethylene 660 12-hydroxystearate (Solutol HS15).

Polymers Having a Mucoadhesive Effect

The matrix layer further comprises polymers having a mucoadhesive effect. Suitable polymers having a mucoadhesive effect are in particular a chitosan (chitosan and derivatives, chitosans), (meth)acrylate copolymers consisting of 20-45% by weight methyl methacrylate and 55 to 80% by weight methacrylic acid, celluloses, especially methyl celluloses such as Na carboxymethylcellulose (e.g. Blanose® or Methocel®).

The polymer having a mucoadhesive effect is chosen so that it exhibits a water uptake of from 10 to 750, preferably 10 to 250, particularly preferably 10 to 160, % in 15 min in a range of +/−0.5, preferably +/−0.3, pH units relative to the pH at which the outer coating starts to dissolve.

Measurement of the Mucoadhesive Properties

A suitable measurement method for characterizing mucoadhesive properties is contained in Hassan and Gallo (1990) (see Hassan E. E. and Gallo J. M. "A Simple Rheological Method for the in Vitro Assessment of Mucin-Polymer Bioadhesive Bond Strength" Pharma Res. 7(5), 491 (1990)). The method is based on the assumption that the viscosity (η, dynamic viscosity or viscosity coefficient) of a mixture of polymers with mucin is different from the total of the viscosities of the individual components. The relationship applying is $\eta_{mixture\ of\ polymer\ with\ mucin} = \eta_{mucin} + \eta_{polymer} + \eta_b$, where $\eta_b$ stands for the difference. A higher $\eta_b$ means greater mucoadhesive properties. The individual components are initially measured for their viscosity using a rotational viscometer. A 0.5% strength (w/w) aqueous solution of the mucoadhesive polymer and a 15% strength solution of porcine gastric mucin are employed. To determine the mucoadhesive properties $\eta_b$, mucin and polymer are measured alone and mixed in the stated concentrations.

The polymer having a mucoadhesive effect is chosen so that it exhibits a mucoadhesive effect measured as viscosity $\eta_b$ of from 150 to 1000, preferably 150 to 600, mPa·s in a range of +/−0.5, preferably +/−0.3, pH units relative to the pH at which the outer coating starts to dissolve.

Hydration and Water Uptake

The hydration of polymers is based on the affinity of the polymer to take up water. Polymers swell owing to this water uptake. This is concerned with an imbalance between the chemical potential of the water in the polymer and the water in the surrounding medium. The water is taken up, owing to the osmotic pressure of the polymer, until an equilibrium is set up between inner and outer phase. The polymer is then 100% hydrated. Polymers having a low average molecular weight are then in the form of a solution. A gel is produced with polymers having a higher molecular weight or crosslinked polymers. The water uptake until the equilibrium is set up may amount for example to up to 10 times the inherent weight, corresponding to 1000% of the polymer weight.

Measurement of the Percentage Water Uptake

Measurement of the percentage water uptake is familiar to the skilled worker. A suitable method is described for example in the Lehrbuch der pharmazeutischen Technologie/ Rudolf Voigt, Basel: Verlag Chemie, 5$^{th}$ completely revised edition, 1984, page 151, 7.7.6 under "Aufsaugvermogen". The method makes use of the so-called Enslin apparatus, in which a glass suction filter funnel is connected by tubing to a graduated pipette. The pipette is mounted exactly horizontally in such a way that it is at the same level as the glass frit. A water uptake of 100% is defined in the present case as a water uptake of 1 ml of water per 1 g of polymer having a mucoadhesive effect in 15 min.

The comparatively rapid water uptake or hydration and the high degree of hydration ensure, at the time at which the outer coating starts to dissolve, a rapid protection of the active substance and a direct binding to the intestinal mucosa. The binding of the active substance in the mucoadhesive matrix should be only small, so that the active substance can pass directly from the intestinal mucosa into the body.

Control of the Matrix pH

The mucoadhesive effect is pH-dependent for many mucoadhesive polymers. The pH in the matrix can be specifically controlled through the addition of an acid, of a base or of a buffer system. The inner matrix may comprise as polymer having a mucoadhesive effect for example a chitosan which is employed together with an acetate buffer system. The acetate/Na acetate buffer, e.g. adjusted to pH 5.0 to 5.5, can be present as an additive in the matrix or be applied to a core onto which the matrix is applied. It is possible in this way to employ chitosan also in combination with film coatings which start to dissolve at higher pH values, e.g. pH 6.0 to 8.0. Despite the high surrounding pH, the low pH is maintained in the microenvironment of the matrix. It is thus possible to utilize the mucoadhesive properties of the polymer in a pH range in which it would otherwise have no mucoadhesive effect or not to this extent. This has the advantage that a certain protection against proteases whose pH optimum is in higher pH ranges can be achieved. The same principle can also be applied in the converse manner by raising the pH of the matrix by adding a base, and combining with a film coating which dissolves at lower pH values.

Examples of the Selection of Suitable Mucoadhesive Polymers

The selection of suitable mucoadhesive polymers is based on their mucoadhesive properties and their water uptake capacity. The polymers should have a mucoadhesive effect of at least $\eta_b$=150 to 1000 mPa·s and a water uptake of from 10 to 750% in 15 min in the respective pH range. The following table gives a list by way of example.

Chitosan is suitable for example for use in a surrounding pH region of pH 5.5 (duodenum) or at another surrounding pH region (ileum or colon) as long as the matrix pH region has been adjusted, e.g. with the aid of a buffer system, to the region around pH 5.5.

The (meth)acrylate copolymer listed in the table is more suitable for a pH region of pH 7.2 than for a pH region around pH 5.5.

Na alginate is suitable for the pH region around pH 5.5 but not for pH 7.2.

Na carboxymethylcellulose and crosslinked polyacrylic acid are suitable over a wide pH range from 5.5 to 7.2.

| Mucoadhesive polymer | Mucoadhesive effect $\eta_b$ [mPa·s] at pH 5.5 | Mucoadhesive effect $\eta_b$ [mPa·s] at pH 7.2 | $H_2O$ uptake [% in 15 min] at pH 5.5 | $H_2O$ uptake [% in 15 min] at pH 6.0 | $H_2O$ uptake [% in 15 min] at pH 7.2 |
|---|---|---|---|---|---|
| Chitosan | 220 | 0 | 140 | 320 | 320 |
| (Meth)acrylate copolymer* | 150 | 480 | 170 | 50 | 125 |
| Na alginate | 580 | 0 | 40 | 50 | 50 |
| Na carboxymethylcellulose | 300 | 250 | 55 | 50 | 50 |
| Polyacrylic acid crosslinked | 350 | 340 | 50 | 25 | 25 |

*(Meth)acrylate copolymer of 30% by weight methyl methacrylate and 70% by weight methacrylic acid The Outer Coating of Anionic (Meth)Acrylate Copolymers The outer coating of anionic polymers or copolymers serves as coating resistant to gastric juice in order to protect the inner matrix layer from gastric juices. The outer coating additionally acts to protect the active substance from proteolytic enzymes until the time when the coating reaches a section of the intestine (duodenum, jejunum, ileum or colon) where it starts to dissolve. The outer coating serves in this case in particular for so-called "gastrointestinal targeting", i.e. the targeted release of the inner matrix layer at the sections of the intestine determined by the pH prevailing there. For there to be no impediment to the delivery of the inner matrix layer, the (meth)acrylate copolymer of the outer coating should exhibit minimal or only slight interactions with the active substance or the mucoadhesive polymer of the inner matrix layer.

Suitable anionic polymers or copolymers are cellulose glycolate (Duodcell®), cellulose acetate phthalate (CAP, Cellulosi acetas, PhEur, cellulose acetate phthalates, NF, Aquateric®), cellulose acetate succinate (CAS), cellulose acetate trimeliate (CAT), hydroxypropylmethylcellulose phthalate (HPMCP, HP50, HP55), hydroxypropylmethylcellulose acetate succinate (HPMCAS-LF, -MF, -HF), polyvinyl acetate phthalate (PVAP, Sureteric®), vinyl acetate-vinylpyrrolidone copolymer (PVAc, Kollidon® VA64), vinyl acetate: crotonic acid 9:1 copolymer (VAC:CRA, Kollicoat® VAC) and/or shellack. Said polymers and copolymers can in many cases be formulated in a perfectly satisfactory way to allow pH-specific dissolution to be achieved.

The outer film coating particularly preferably consists essentially of (meth)acrylate copolymers having a content of monomers having anionic groups of from 5 to 60% by weight, which may optionally be formulated with pharmaceutically usual excipients, especially plasticizers. Compared with the polymers mentioned at the outset, said anionic (meth)acrylate copolymers make it possible within the scope of the invention in many cases for the pH-specific adjustment of the dissolution pH to be adjusted even more accurately and reproducibly. The handling and application is also usually regarded as less elaborate.

(Meth)acrylate copolymer for the outer coating preferably consists of 40 to 95, preferably 45 to 90, in particular 30 to % by weight of free-radical polymerized $C_1$- to $C_4$-alkyl esters of acrylic or of methacrylic acid and may comprise from 5 to 60, preferably 8 to 40, in particular 20 to 35, % by weight of (meth)acrylate monomers having an anionic group.

The proportions mentioned normally add up to 100% by weight. However, it is possible in addition, without this leading to an impairment or alteration of the essential properties, for small amounts in the region of from 0 to 10, e.g. 1 to 5% by weight of further monomers capable of vinylic copolymerization, such as, for example, hydroxyethyl methacrylate or hydroxyethyl acrylate, to be present.

$C_1$- to $C_4$-Alkyl esters of acrylic or methacrylic acid are in particular methyl methacrylate, ethyl methacrylate, butyl methylacrylate, methyl acrylate, ethyl acrylate and butyl acrylate.

A (meth)acrylate monomer having an anionic group may for example be acrylic acid, but preferably methacrylic acid.

Also suitable are anionic (meth)acrylate copolymers composed of from 40 to 60% by weight methacrylic acid and 60 to 40% by weight methyl methacrylate or 60 to 40% by weight ethyl acrylate (Eudragit® L or Eudragit® L100-55).

Eudragit® L is a copolymer of 50% by weight methyl methacrylate and 50% by weight methacrylic acid. Eudragit® L 30D is a dispersion comprising 30% by weight Eudragit® L. This (meth)acrylate copolymer is particularly suitable for dissolution in pH ranges around pH 6.0 to 6.5 (jejunum).

Eudragit® L100-55 is a copolymer of 50% by weight ethyl acrylate and 50% by weight methacrylic acid. Eudragit® L 30-55 is a dispersion comprising 30% by weight Eudragit® L 100-55. This (meth)acrylate copolymer is particularly suitable for dissolution in pH ranges around pH 5.5 to 6.0 (duodenum).

Likewise suitable are anionic (meth)acrylate copolymers of 20 to 40% by weight methacrylic acid and 80 to 60% by weight methyl methacrylate (Eudragit® S type). This (meth)acrylate copolymer is particularly suitable for dissolution in pH ranges around pH 6.5 to 7.0 (jejunum and ileum).

Particularly suitable (meth)acrylate copolymers are those consisting of 10 to 30% by weight methyl methacrylate, 50 to 70% by weight methyl acrylate and 5 to 15% by weight methacrylic acid.

Eudragit® FS is a copolymer of 25% by weight methyl methacrylate, 65% by weight methyl acrylate and 10% by weight methacrylic acid. Eudragit® FS 30 D is a dispersion comprising 30% by weight Eudragit® FS. This (meth)acrylate copolymer is particularly suitable for dissolution in pH ranges around pH 7.0 to 7.8 (ileum and colon).

Additionally suitable is a copolymer composed of
20 to 34% by weight methacrylic acid and/or acrylic acid,
20 to 69% by weight methyl acrylate and
0 to 40% by weight ethyl acrylate and/or where appropriate
0 to 10% by weight further monomers capable of vinylic copolymerization,
with the proviso that the glass transition temperature of the copolymer according to ISO 11357-2, subsection 3.3.3, is not more than 60° C. This (meth)acrylate copolymer is particularly suitable, because of its good elongation at break properties, for compressing pellets to tablets.

Additionally suitable are copolymers composed of
20 to 33% by weight methacrylic acid and/or acrylic acid,
5 to 30% by weight methyl acrylate and
20 to 40% by weight ethyl acrylate and
more than 10 to 30% by weight butyl methacrylate and where appropriate
0 to 10% by weight further monomers capable of vinylic copolymerization,
where the proportions of the monomers add up to 100% by weight,
with the proviso that the glass transition temperature of the copolymer according to ISO 11357-2, subsection 3.3.3 (midpoint temperature $T_{mg}$), is 55 to 70° C. Copolymers of this type are particularly suitable, because of its good mechanical properties, for compressing pellets to tablets.

The abovementioned copolymer is composed in particular of free-radical polymerized units of
20 to 33, preferably 25 to 32, particularly preferably 28 to 31, % by weight methacrylic acid or acrylic acid, with preference for methacrylic acid,
5 to 30, preferably 10 to 28, particularly preferably 15 to 25, % by weight methyl acrylate,
20 to 40, preferably 25 to 35, particularly preferably 18 to 22, % by weight ethyl acrylate, and
more than 10 to 30, preferably 15 to 25, particularly preferably 18 to 22, % by weight butyl methacrylate,
where the monomer composition is chosen so that the glass transition temperature of the copolymer is from 55 to 70° C., preferably 59 to 66, particularly preferably 60 to 65° C.

It is also possible to employ mixtures of the copolymers mentioned in order to adjust specific release profiles or release sites.

Glass transition temperature means in this connection in particular the midpoint temperature $T_{mg}$ according to ISO 11357-2, subsection 3.3.3. The measurement takes place without added plasticizer, with residual monomer contents (REMO) of less than 100 ppm, with a heating rate of 10° C./min and under a nitrogen atmosphere.

The copolymer preferably consists essentially to exclusively of 90, 95 or 99 to 100% by weight of the monomers methacrylic acid, methyl acrylate, ethyl acrylate and butyl methacrylate in the ranges of amounts indicated above.

However, it is possible, without this necessarily leading to an impairment of the essential properties, for small amounts in the range from 0 to 10, e.g. 1 to 5% by weight of further monomers capable of vinylic copolymerization additionally to be present, such as, for example, methyl methacrylate, butyl acrylate, hydroxyethyl methacrylate, vinylpyrrolidone, vinylmalonic acid, styrene, vinyl alcohol, vinyl acetate and/or derivatives thereof.

The copolymers are obtained in a manner known per se by free-radical bulk, solution, bead or emulsion polymerization. Before processing, they must be brought to the particle size range of the invention by suitable grinding, drying or spraying processes. This can take place by simple crushing of extruded and cooled pellets or hot cut.

The use of powders may be advantageous especially on mixture with other powders or liquids. Suitable apparatuses for producing powders are familiar to the skilled worker, e.g. air jet mills, pinned disc mills, compartment mills. It is possible where appropriate to include appropriate sieving steps. A suitable mill for industrial large quantities is for example an opposed jet mill (Multi No. 4200) which is operated with a 6 bar overpressure.

Copolymer Preparation

Said (meth)acrylate copolymers can be obtained by free-radical polymerization of the monomers (see, for example, EP 0 704 207 A2 and EP 0 704 208 A2). The copolymers can be prepared in a manner known per se by free-radical emulsion polymerization in aqueous phase in the presence of, preferably, anionic emulsifiers, for example by the process described in DE-C 2 135 073.

Organic Solution

Said (meth)acrylate copolymers can be provided in the form of an organic solution, e.g. in a concentration of from 10 to 30% by weight. Examples of solvents which can be used are acetone, isopropanol or ethanol or mixture thereof, which may where appropriate comprise water in proportions up to about 10% by weight. However, aqueous dispersions are preferred.

Dispersions

Said (meth)acrylate copolymers can be produced and used as emulsion polymers, preferably in the form of a 10 to 50 percent by weight, in particular 20 to 40 percent strength, aqueous dispersion. A solids content of 30% by weight is preferred as commercial form. Partial neutralization of the methacrylic acid units can be dispensed with for processing; it is, however, possible, for example to an extent of up to 5 or 10 mol %, if stabilization or thickening of the coating composition dispersion is desired. The weight average size of the latex particles is ordinarily from 40 to 100 nm, preferably 50 to 70 nm, thus ensuring a viscosity of below 1000 mPa·s, which is favorable for processing.

With higher degrees of neutralization, e.g. 10 to 50 mol % or complete neutralization, it is possible for the copolymer to be converted into a dissolved state.

In order to prepare a solution of the anionic copolymer, it is usually necessary to neutralize the acidic groups partly or completely. The anionic copolymer may for example be stirred gradually into water in a final concentration of from 1 to 40% by weight and at the same time be partly or completely neutralized by adding a basic substance such as, for example, NaOH, KOH, ammonium hydroxide or organic bases such as, for example, triethanolamine. It is also possible to employ a powder of the copolymer to which a base, e.g. NaOH, has been added during its preparation for the purpose of (partial) neutralization, so that the powder is a polymer which is already (partly) neutralized. The pH of the solution is usually above 4, e.g. in the range from 4 to about 7.

The dispersion can for example also be spray dried or freeze dried in a manner known per se and be provided in the form of a redispersible powder (see, for example, EP-A 0 262 326). Alternative processes are freeze drying or coagulation and squeezing out of the water in an extruder with subsequent granulation (see, for example, EP-A 0 683 028).

It has surprisingly been found that copolymer dispersions from spray- or freeze-dried and redispersed powders exhibit increased shear stability. This is advantageous in particular in the case of spray application. This advantage is particularly evident when the copolymer present in the dispersion is partly neutralized to the extent of 2 to 10 mol % (based on the acidic groups present in the copolymer). Partial neutralization by adding NaOH is preferred for this purpose. An anionic emulsifier is preferably present in an amount of from 0.1 to 2% by weight. Sodium lauryl sulfate is particularly preferred as emulsifier.

Layer Thicknesses

The layer thickness of the outer coating is preferably in the range from 20 to 200, preferably from 50 to 120 μm.

Production of a Multiparticulate Pharmaceutical Form

The invention additionally relates to a process for producing a multiparticulate pharmaceutical form by a) producing an inner matrix layer comprising an active substance, which is a peptide or protein, and a polymer having a mucoadhesive effect and, where appropriate, further pharmaceutically usual excipients by means of spray application onto a core or by rotagglomeration, precipitation or spray processes without a core, and subsequently b) applying an outer film coating consisting essentially of an anionic polymer, which may optionally be formulated with pharmaceutically usual excipients, especially plasticizers, by means of spray application so that active substance-containing, enveloped pellets are obtained, and c) processing the resulting pellets by means of pharmaceutically usual excipients in a manner known per se to a multiparticulate pharmaceutical form, in particular to pellet-containing tablets, minitablets, capsules, sachets or reconstitutable powders, which are formulated so that the contained pellets are released in the pH range of the stomach.

Production of Prepellets and Pellets

The pelleting can take place onto active substance-free beads (nonpareilles), or core-free pellets can be produced.

Firstly, the inner matrix layer with or without core is produced. This as yet uncoated, rounded layer referred to as prepellet (pellet core).

It is possible by means of a fluidized bed process to apply the liquid to placebo pellets or other suitable carrier materials, with evaporation of the solvent or suspending agent. A drying step may follow the production process.

The peptide or protein active substance is introduced with the polymer having a mucoadhesive effect into an organic solvent or into water and mixed. In order to ensure satisfactory sprayability of the mixture, it is usually necessary to formulate a mixture of low viscosity. It may be beneficial for this purpose to employ the polymer having mucoadhesive effect in comparatively low concentrations, e.g. from 1 to a maximum 10, preferably 2 to 5, % by weight. Addition of a detergent, e.g. Tween, in concentrations of from 0.1 to 20, preferably 0.5 to 10% by weight may moreover be advantageous to reduce the surface tension.

They may, besides the active substance, comprise further pharmaceutical excipients: binders such as cellulose and derivatives thereof, polyvinylpyrrolidone (PVP), humectants, disintegration promoters, lubricants, disintegrants, (meth)acrylates, starch and derivatives thereof, sugar solubilizers or others.

Appropriate application processes are disclosed for example in Bauer, Lehmann, Osterwald, Rothgang, "Überzogene Arzneiformen" Wissenschaftliche Verlagsgesellschaft mbH Stuttgart, chapter 7, pp. 165-196.

Details are furthermore disclosed to the skilled worker in texts books. See, for example:

Voigt, R. (1984): Lehrbuch der pharmazeutischen Technologie; Verlag Chemie Weinheim—Beerfield Beach/Florida—Basel.

Sucker, H., Fuchs, P., Speiser, P.: Pharmazeutische Technologie, Georg Thieme Verlag Stuttgart (1991), especially chapters 15 and 16, pp. 626-642.

Gennaro, A. R. (editor), Remington's Pharmaceutical Sciences, Mack Publishing Co., Easton Pa. (1985), Chapter 88, pp. 1567-1573.

List, P. H. (1982): Arzneiformenlehre, Wissenschaftliche Verlagsgesellschaft mbH, Stuttgart.

The inner matrix may also be produced without the assistance of an inert core (nonpareilles). The ingredients of the inner matrix may in this case be rounded to as yet uncoated pellets (prepellets) of defined size, e.g. 50 to 1000 μm, by processes such as rotagglomeration, precipitation or spray processes, especially ultrasound fluidized spray processes. This has the advantage that the entire core volume is available for loading with active substance. The loading with active substance can thus be increased further compared with the embodiment having an inert core.

After production of the inner matrix cores (or of the pre-pellets), they are in turn provided, preferably in the spray process, with the outer coating, to result in finished pellets. The pellets are produced by spray application from organic solution, or preferably from aqueous dispersions. It is decisive for implementation in this case that uniform, pore-free coatings are produced.

Topcoat

The pellets can additionally be provided with pigmented coatings which, however, must not influence the dissolution pH. Suitable examples are coatings composed of pigmented hydroxypropylmethylcellulose or other polymers which are soluble in water or rapidly disintegrate in water.

Pharmaceutically Usual Excipients

Usual excipients or additives can be added to the formulations of the invention during production. It is, of course, always necessary for all the substances employed to be toxicologically acceptable and usable in particular in medicaments without a risk for patients.

The amounts employed and the use of the usual additives in medicament coatings or layerings are familiar to the skilled worker. Possible examples of usual additives are plasticizers, release agents, pigments, stabilizers, antioxidants, pore formers, penetration promoters, gloss agents, aromatizing substances, detergents, lubricants or flavorings. They serve as processing aids and are intended to ensure a reliable and reproducible production process and good long-term storage stability, or they achieve additional advantageous properties in the pharmaceutical form. They are added to the polymer preparations before the processing and may influence the permeability of the coatings, it being possible to utilize this where appropriate as additional control parameter.

Release Agents:

Release agents usually have lipophilic properties and are usually added to the spray suspensions. They prevent agglomeration of the cores during the film coating. Talc, Mg stearate or Ca stearate, ground silica, kaolin or nonionic emulsifiers having an HLB of between 3 and 8 are preferably employed. The usual amounts employed of release agent in the coating agents and binders of the invention are between 0.5 to 100% by weight based on the copolymer.

Pigments:

Pigments incompatible with the coating agent are in particular those pigments which, if added directly to the (meth) acrylate copolymer dispersion, e.g. by stirring in, in the usual amounts used of, for example, 20 to 400% by weight based on the dry weight of the (meth)acrylate copolymer, lead to destabilization of the dispersion, coagulation, to signs of inhomogeneity or similarly unwanted effects. The pigments to be used are moreover of course non-toxic and suitable for pharmaceutical purposes. Concerning this, see also, for example: Deutsche Forschungsgemeinschaft, *Farbstoffe für Lebensmittel*, Harald Boldt Verlag K G, Boppard (1978); Deutsche Lebensmittelrundschau 74, No. 4, p. 156 (1978); Arzneimittelfarbstoffverordnung AmFarbV of Aug. 25, 1980.

Pigments incompatible with the coating agent may be for example alumina pigments. Examples of incompatible pigments are orange yellow, cochineal red lake, colored pigments based on alumina or azo dyes, sulfonic acid dyes, orange yellow S (E110, C.I. 15985, FD&C Yellow 6), indigo carmine (E132, C.I. 73015, FD&C Blue 2), tartrazine (E 102, C.I. 19140, FD&C Yellow 5), ponceau 4R (E 125, C.I. 16255, FD&C Cochineal Red A), quinoline yellow (E 104, C.I. 47005, FD&C Yellow 10), erythrosine (E127, C.I. 45430, FD&C Red 3), azorubine (E 122, C.I. 14720, FD&C Carmoisine), amaranth (E 123, C.I. 16185, FD&C Red 2), acid brilliant green (E 142, C.I. 44090, FD&C Green S).

The E numbers indicated for the pigments relate to an EU numbering. Concerning this, see also "Deutsche Forschungsgemeinschaft, Farbstoffe, für Lebensmittel, Harald Boldt Verlag K G, Boppard (1978); Deutsche Lebensmittelrundschau 74, No. 4, p. 156 (1978); Arzneimittelfarbstoffverordnung AmFarbV of Aug. 25, 1980. The FD&C numbers relate to the approval in Food, Drugs and Cosmetics by the U.S. Food and Drug Administration (FDA) described in: U.S. Food and Drug Administration, Center for Food Safety and Applied Nutrition, Office of Cosmetics and Colors: Code of Federal Regulations—Title 21 Color Additive Regulations Part 82, Listing of Certified Provisionally Listed Colors and Specifications (CFR 21 Part 82).

Plasticizers

Further additives may also be plasticizers. The usual amounts are between 0 and 50, preferably 2 to 20, in particular 5 to 10% by weight.

Plasticizers may influence the functionality of the polymer layer, depending on the type (lipophilic or hydrophilic) and added amount. Plasticizers achieve through physical interaction with the polymers a reduction in the glass transition temperature and promote film formation, depending on the added amount. Suitable substances usually have a molecular weight of between 100 and 20 000 and comprise one or more hydrophilic groups in the molecule, e.g. hydroxyl, ester or amino groups.

Examples of suitable plasticizers are alkyl citrates, glycerol esters, alkyl phthalates, alkyl sebacates, sucrose esters, sorbitan esters, diethyl sebacate, dibutyl sebacate and polyethylene glycols 200 to 12 000. Preferred plasticizers are triethyl citrate (TEC) and acetyl triethyl citrate (ATEC). Mention should additionally be made of esters which are usually liquid at room temperature, such as citrates, phthalates, sebacates or castor oil. Esters of citric acid and sebacic acid are preferably used.

Addition of plasticizers to the formulation can take place in a known manner, directly, in aqueous solution or after thermal pretreatment of the mixture. It is also possible to employ mixtures of plasticizers.

Production of Multiparticulate Pharmaceutical Forms

The active substance-containing coated pellets can be processed by means of pharmaceutically usual excipients and in a manner known per se to multiparticulate pharmaceutical forms, in particular to pellet-containing tablets, minitablets, capsules, sachets or powders for reconstitution, which are formulated such that the contained pellets are released in the pH range of the stomach. The preparation as multiparticulate pharmaceutical form places a high dosage reliability offers the advantage of good distribution of the pellets in the intestinal lumen. The multiparticulate pharmaceutical form of the invention may additionally also comprise different pellet types with different active substances and/or different pellet structure.

Compressed Tablets

The production of multiparticulate pharmaceutical forms by compression of a pharmaceutically usual binder with active ingredient-containing particles is described for example in Beckert et al. (1996), "Compression of enteric-coated pellets to disintegrating tablets", *International Journal of Pharmaceutics* 143, pp. 13-23, and in WO 96/01624.

Film coatings on active substance-containing pellets are normally applied in fluidized bed apparatuses. Formulation examples are mentioned in this application. Film formers are normally mixed with plasticizers and release agents by a suitable process. It is possible in this case for the film formers to be in the form of a solution or suspension. The excipients for film formation may likewise be dissolved or suspended. Organic or aqueous solvents or dispersing agents can be used. Stabilizers can be used additionally to stabilize the dispersion (example: Tween 80 or other suitable emulsifiers or stabilizers).

Examples of release agents are glycerol monostearate or other suitable fatty acid derivatives, silica derivatives or talc. Examples of plasticizers are propylene glycol, phthalates, polyethylene glycols, sebacates or citrates, and other substances mentioned in the literature.

A separating layer can be applied between active substance-containing and intestine-soluble copolymer layer and serves to separate active substance and coating material for the purpose of preventing interactions. This layer may consist of inert film formers (e.g. HPMC, HPC or (meth)acrylic acid copolymers) or, for example, talc or another suitable pharmaceutical substances. It is likewise possible to use combinations of film formers and talc or similar substances. It is also possible to apply a separating layer composed of partially or completely neutralized (meth)acrylate copolymer dispersions.

The separating layer may also consist of the same or a different mucoadhesive polymer as in the underlying matrix layer. Possible interactions or incompatibilities of the active substance or of the mucoadhesive polymer with the film-forming (meth)acrylate copolymer layer can be countered in this way.

Mixtures for producing tablets composed of coated particles are prepared by mixing the pellets with suitable binders for tableting, if necessary adding disintegration-promoting substances and if necessary adding lubricants. The mixing can take place in suitable machines. Unsuitable mixers are those leading to damage to the coated particles, e.g. plowshare mixers. To achieve suitable short disintegration times it may be necessary to add the excipients to the coated particles in a specific sequence. It is possible by premixing with the coated particle with the lubricant or mold release agent magnesium stearate for its surface to be rendered hydrophobic and thus for adhesion to be avoided.

Mixtures suitable for tableting normally comprise 3 to 15% by weight of a disintegration aid, e.g. Kollidon C L and, for example, 0.1 to 1% by weight of a lubricant and mold release agent such as magnesium stearate. The proportion of binder is determined by the required proportion of coated particles.

Examples of typical binders are Cellactose®, microcrystalline cellulose, calcium phosphates, Ludipress®, lactose or other suitable sugars, calcium sulfates or starch derivatives. Substances of low bulk density are preferred.

Typical disintegration aids (disintegrants) are crosslinked starch derivatives or cellulose derivatives, and crosslinked polyvinylpyrrolidone. Cellulose derivatives are likewise suitable. It is possible to dispense with the use of disintegration aids through selection of a suitable binder.

Typical lubricants and mold release agents are magnesium stearates or other suitable salts of fatty acids or substances detailed in the literature for this purpose (e.g. lauric acid, calcium stearate, talc, etc.). It is possible to dispense with the use of a lubricant and mold release agent in the mixture on use of suitable machines (e.g. tablet press with external lubrication) or suitable formulations.

It is possible where appropriate to add an aid to the mixture to improve the flow (e.g. colloidal silica derivatives, talc, etc.).

The tableting can take place on usual tablet presses, eccentric or rotary tablet presses, with compressive forces in the range from 5 to 40 kN, preferably 10-20 kN. The tablet presses can be equipped with systems for external lubrication. Special systems for die filling, which avoid die filling by means of impeller paddles, are employed where appropriate.

Further Multiparticulate Pharmaceutical Forms

As an alternative to compressed tablets or minitablets, it is also possible for the active substance-containing coated pellets to be processed to any other orally administered multiparticulate pharmaceutical form. The coated pellets can, for example, be packed into capsules, e.g. gelatin capsules, or formulated to sachets or reconstitutable powders.

Advantageous Effects of the Invention

The pharmaceutical form of the invention is suitable for targeted and efficient release of protein or peptide active substances. The pharmaceutical form exhibits a high dosage reliability and distributes well in the intestinal lumen. The contained protein or peptide active substance is moreover substantially protected from physical or proteolytic inactivation and can be released at the defined site of action in such a way that a high proportion of the active substance can be taken up by the body. The pharmaceutical form therefore makes do with less active substance, because only a little of the active substance is lost. The risk of side effects is reduced overall by the targeted delivery. The site of action can be adjusted variably, depending on the therapeutic aim. The timing of the active substance uptake can thus be better controlled. Because the pharmaceutical form is for oral use it is accepted better overall by patients (patient compliance) compared with other administration forms. A large number of peptide or protein active substances can thus be made available for oral use for the first time and the risks of administration are often less than with parenteral administration in particular. The costs of administration can also be kept low because no skilled staff are necessary for the administration.

An accelerated release with, at the same time, an increase in the bioavailability can be achieved from matrix systems in which the proportion of the polymer having a mucoadhesive effect in % by weight is 3 times, preferably 1000 times higher than the proportion of active substance.

Lipophilic Matrix

A special aspect of the invention emerges when the active substance has been embedded into a lipophilic matrix which has a melting point above 37° C., preferably above 45° C., particularly preferably preferably above 55° C., and the active substance-containing lipophilic matrix has been embedded into the matrix composed of the polymer having a mucoadhesive effect. The aim of formulation in the lipophilic matrix is to improve the solubility and the bioavailability of the active substance, preferably of sparingly or slightly soluble active substances (as defined in DAB 10, 2003).

A lipophilic matrix means in the context of the invention a substance or a mixture of substances in which the active substance can be dissolved, suspended or emulsified. The substance or the substances of the lipophilic matrix are different from the usual pharmaceutical excipients and the polymer having a mucoadhesive effect. The substance or the substances of the lipophilic matrix preferably have a hydrophobic or else amphiphilic character. The lipophilic matrix might also be referred to as amphiphilic matrix or as lipoidal matrix.

The lipophilic matrix may consist of a single substance, e.g. of a lipid, or of a mixture of substances, e.g. of a mixture of lipids. In the case of mixtures, the properties described hereinafter for water solubilities according to DAB 10, partition coefficients and/or HLB values are calculated in each case from the arithmetic mean of the parts by weight and the values of the substances of the mixture. The employed substances must not be toxic.

The active substance and the substance or substances forming the lipophilic matrix preferably differ in their solubility in water according to DAB 10 and not more than +/−50%, preferably do not differ more than +/−25%, and/or differ in their partition coefficient according to annex V to directive 67/548/EEC, A.8 not more than +/−60%, preferably not more than +/−30%, and/or differ in their HLB, if an HLB can be assigned to the substances, measured by the Marszall method, not more than +/−80%, preferably not more than +/−40%. A greater agreement of the active substance with the lipophilic matrix in at least one, preferably two or all three of said properties, means a greater favoring of the solubility and the bioavailability of the active substance in the pharmaceutical form.

Solubility in Water

The solubility in water for the active substance and the substance or substances forming the lipophilic matrix can be defined as specified in DAB 10 (Deutsches Arzneibuch, $10^{th}$ edition with $3^{rd}$ supplement 1994, Deutscher Apothekerverlag, Stuttgart und Govi Verlag, Frankfurt/Main, $2^{nd}$ supplement (1993), IV Allgemeine Vorschriften, pp. 5-6, "Löslichkeit und Lösungsmittel"; see also Ph. Eur. Jul. 4, 2004). The solubility is defined by the number of parts by volume of solvent for 1 part by weight of substance or drug. The definition of "sparingly soluble" includes substances which require from 30 to 100 parts by volume of solvent for 1 part by weight of substance or drug, and the definition of "slightly soluble" includes substances which require from 100 to 1000 parts by volume of solvent for 1 part by weight of substance or drug.

Partition Coefficients

The partition coefficients for the active substance and the substance or substances forming the lipophilic matrix can be determined in accordance with annex V to directive 67/548/EEC, A.8 "partition coefficient".

HLB

The HLB is a measure, introduced by Griffin in 1950, of the hydrophilicity or lipophilicity of nonionic surfactants. It can be determined experimentally by the phenol titration method of Marszall; cf. "Parfümerie, Kosmetik", volume 60, 1979, pp. 444-448; further references in Römpp, Chemie-Lexikon, $8^{th}$ edition, 1983, p. 1750. See also, for example, U.S. Pat. No. 4,795,643 (Seth)). An HLB (hydrophile/lipophile balance) can be determined accurately only for nonionic substances. With anionic substances it is possible to determine this value by calculation, but it is virtually always above or far above 14.

HLB values for the active substance and the substance or substances forming the lipophilic matrix can in most cases be determined by the method of Marszall, be taken from tables of pharmaceutical or chemical reference works or text books or, in the case of ionic substances, be determined by calculation.

Active Substances in the Lipophilic Matrix

The pharmaceutical form preferably comprises in the lipophilic matrix an active substance which has a solubility in water according to DAB 10 of at least 30, in particular from 30 to 100 or from 100 to 1000 parts by volume of water for one part by weight of active substance. The preferred active substance is accordingly sparingly or even slightly soluble according to the DAB 10 definition.

The active substance formulated in the lipophilic matrix may be selected for example from the group of peptide antibiotics, immunosuppressants, LHRH antagonists, immunomodulators.

The active substance formulated in the lipophilic matrix may be for example abarelix, angiotensin II, anidulafungin, antide, argipressin, azaline and azaline B, bombesin antagonist, bradykinin, buserelin, calcitonin, cetrorelix, cyclosporin, cyclosporin A, desmopressin, detirelix, erythropoietin, encephalins (Leu-, Met-) ganirelix, gonadorelin, goserelin, growth hormone secretagogue, insulin, interferon (alpha, beta, gamma), interleukins (IL1, IL2), micafungin, nafarelin, leuprolide, leuprorelin, octreotide, orntide, oxytocin, parathyroid hormone, ramorelix, secretin, somatotropin, terlipressin, tetracosactide, teverelix, triptorelin, thyroliberin, thyrotropin tumor necrosis factor (TNF alpha, beta), or vasopressin.

Lipophilic Matrix/Polymers Having a Mucoadhesive Effect

In a preferred embodiment, possible interactions of the lipophilic matrix with the polymer having a mucoadhesive effect are taken into account. In order to avoid uncontrollable interactions, the substance or the substances which form the lipophilic matrix, and the polymer having a mucoadhesive effect should preferably either have the same ionic properties, i.e. both should have concordantly either at least predominantly cationic or concordantly anionic character. In the event that substances having opposed ionic properties are selected, the polymer having a mucoadhesive effect should preferably be present in at least 50, particularly preferably 100%, neutralized form. The neutralization can take place by adding acid or base in a known manner.

Substance or Substances for Assembling the Lipophilic Matrix

The lipophilic matrix preferably consists of 80 to 100, preferably 90 to 100, particularly preferably 100% by weight of a substance or of a mixture of substances having an (averaged) HLB of from 0 to 15, preferably 2 to 10 consists. The lipophilic matrix may comprise 0 to 20, preferably 0 to 10% by weight of pharmaceutically usual excipients, especially stabilizers, thickeners or adsorbents. It is particularly preferred for no pharmaceutically usual excipients to be present.

The substance or the substances which form the lipophilic matrix may for example belong to the group of oils, fats, mono-, di- or triglycerides, fatty acids, fatty alcohols, especially $C_6$ to $C_{20}$ fatty acid and/or a $C_6$ to $C_{20}$ alcohol including their salts, ether, ester or amide derivatives, phospholipids, lecithins, emulsifiers, lipoids, lipid-soluble vitamins or surfactants.

The lipophilic matrix may comprise for example one of the following lipid preparations: (Imwitor 308) glyceryl monocaprylates having a monoester content of >80%, (Imwitor 312) glyceryl monolaurates having a monoester content of >90%, (Imwitor 491) glycerol monostearates ($C_{16}$+$C_{18}$) having a monoester content of >90%, (Imwitor 900 P) glycerol monostearate having a monoester content of 40-55% and a $C_{18}$ content of 40-60%, (Imwitor 900 K) glycerol monostearate, having a monoester content of 40-55% and a $C_{18}$ content of 60-80%, (Imwitor 742) medium chain-length $C_8$ and $C_{10}$ glycerides having a monoester content of 45-55%, (Imwitor 928) partial glycerides of saturated vegetable $C_{10}$-$C_{18}$ fatty acids having a main content of $C_{12}$, and having a monoester content of 34-36%, $C_8$ and $C_{10}$ glycerides, Na caprylate or Na capriate.

The lipophilic matrix may comprise for example one of the following lipid preparations:

fats such as mono-, di-, triglycerides of saturated and unsaturated fatty acids and mixtures thereof. In particular glycerol stearic acid ester, glycerol palmitic acid ester, glycerol myristic acid ester, glycerolpalmitic acid stearic acid ester, glycerol lauric acid ester, glycerol caprylic acid ester, glycerol oleic acid ester, examples of these esters are Imwitor®-308, -312, -491, -742, -900, -928, -988, and Gelucire® 44/14, -50/13, Geleol, Compritol E ATO, Dynasan 114, Softisan, Witepsol, Dynacet 212, coconut fat.

Oils such as, for example, castor oil, sesame oil, sunflower oil, cottonseed oil, corn oil, almond oil, peanut oil, olive oil, coconut oil, carrot oil, wheat germ oil, walnut oil.

Neutral oils such as isopropyl myristate, isopropyl palmitate, isopropyl stearate, medium chain-length triglycerides (Miglyol®).

Short-chain aliphatic and aromatic carboxylic esters such as, for example, dibutyl phthalate, diethyl sebacate, dibutyl sebacate, tributyl citrate, acetyl tributyl citrate, glycerol triacetate.

Waxes such as, for example, canauba wax, beeswax, wool wax

Glycerol behenic acid ester.

Fatty acid amides such as, for example, stearamide, palmitamide, lauramide.

Aliphatic long-chain carboxylic acids such as, for example, stearic acid, palmitic acid, lauric acid, myristic acid, oleic acid, caprylic acid, linoleic acid, linolenic acid. And, for example, their Na, Al and Mg salts.

Fatty alcohols such as, for example, stearyl alcohol, lauryl alcohol, cetyl alcohol, myristin alcohol, glycerol formal.

W/O emulsifiers such as, for example, cholesterol, glycerol monostearate, ethylene glycol monostearate, sorbitan monooleate (Span® 80), sorbitan monopalmitate (Span® 40), sorbitan monolaurate (Span® 20), sorbitan monostearate (Span® 60), sorbitan trioleate (Span® 85), sorbitan tristearate (Span® 65), sorbitan sesquioleates (Arlacel® 83), Ca, Al, Mg stearate, polyoxyethylene sorbitan tristearate (Tween® 65), polyoxyethylene sorbitan trioleate (Tween® 85).

Nonionic O/W emulsifiers such as, for example, macrogol stearate 400 (Chremophor® A), macrogol lauryl ether, polyethylene glycol 20 sorbitan monolaurate, sorbitan monostearate, sorbitan monopalmitate, sorbitan monooleate, macrogol 1500 glycerol triricinoleate, macrogol glycerol hydroxystearate (Cremophor® RH), macrogol 1000 glycerol monolaurate, monostearate, monooleate, sucrose monostearate. Polysorbate 60 (Tween® 60), polyoxyethylene monostearate (Myrj 49), polysorbate 80 (Tween® 80), polysorbate 40 (Tween® 40), polysorbate 20 (Tween® 20), poloxamer 407 (Lutrol® F 127), poloxamer 188 (Lutrol® F 68), polyoxyethylene ricinoleate (Cremophor® EL), polyoxyethylene 5 stearyl stearate.

Ionic O/W emulsifiers such as, for example, cetylstearyl sulfate (Lanette® E), Na lauryl sulfate (Texapon® Z), Na glycocholate, hederagenin.

Amphiphilic emulsifiers such as, for example, egg phosphatidylcholine (egg lecithin), soya phosphatidylcholine (soya lecithin), betaine, sulfobetaines, ceramides (sphingomyelin).

Vitamins such as, for example, retinol (vitamin A), cholecalciferol (vitamin D), alpha-tocopherol and alpha-tocopherol acetate (vitamin E), phylloquinone (vitamin K).

Further excipients are galactolipids such as, for example, monogalactosyl diacylglycerol, digalactosyl diacylglycerol, trigalactosyl diacyl glycerol, and aromatic oils such as, for example, aniseed oil, citronella oil, eucalyptus oil, fennel oil, camomile oil, cardamom oil, pine needle oil, caraway oil, dwarf pine oil, lavender oil, mint oil, muscat oil, clove oil, peppermint oil, rosemary oil, sage oil and terpenes such as, for example, menthol, linalool, 1,4-cineol, pyrethrin, borneol, eudesmol, phytol, manool, azadirachtin, nimbin.

The active substance is preferably at least 10%, particularly preferably at least 20%, especially at least 50%, soluble in the lipophilic matrix.

The content of the active substance-containing lipid matrix in the inner matrix layer a) can be from 1 to 50, preferably 10 to 20% by weight.

The lipophilic matrix preferably comprises at least 50% by weight glycerol monocaprylate, up to 10% by weight Na cholate, up to 10% by weight tocopherol succinate, 1 to 5% by weight of an efflux pump inhibitor in the case where the active ingredient is a substrate of the PgP efflux pump, e.g. Solutol HS 15, a triglyceride, in particular tristearate, with the components adding up to 100%. This lipophilic matrix can be incorporated directly into the mucoadhesive polymer or be emulsified in water and incorporated into the mucoadhesive polymer. In the latter case, the aqueous phase may comprise a weak acid such as, for example, citric acid.

In the case of active substances which are sparingly or even less soluble (according to DAB 10) having a molecular weight of >3000, a protease inhibitor such as, for example, soybean trysin inhibitor is present in the aqueous phase.

Process

The invention also relates to a process for producing a multiparticulate pharmaceutical form with the steps a) production of the active substance-containing lipophilic matrix by suspending and/or dissolving the active substance with the substance(s) which form the lipophilic matrix and, where appropriate, further pharmaceutically usual excipients by vigorously mixing or melting the ingredients, b) production of pre-pellets (pellet cores) by spray application of the mucoadhesive polymer mixed with the active substance-containing lipophilic matrix onto a core or by rotagglomeration, precipitation or spray processes without a core, c) production of pellets by spray application of a coating of the anionic polymer or copolymer, which may optionally comprise admixtures of pharmaceutically usual excipients, especially plasticizers and release agents, from a dispersion or organic solution onto the pre-pellets from step b), d) production of a multiparticulate pharmaceutical form by filling or incorporating the pellets from step c) in a manner known per se, where appropriate with use of pharmaceutically usual excipients, in particular by processing to pellet-containing tablets, minitablets, capsules, sachets or reconstitutable powders.

Preferred Process

Process steps a) and b) are preferably carried out as follows:

a) production of the inner matrix layer by preparing an emulsion, dispersion or solution of the active substance with the substance(s) for the lipophilic matrix, and where appropriate further pharmaceutically usual excipients by vigorously mixing the ingredients in water and producing an oil-in-water preparation having an average particle size of not more than 60, preferably not more than 20 µm, b) production of pre-pellets by spray application of the oil-in-water preparation from step a) onto the mucoadhesive polymer which may optionally comprise admixtures of further pharmaceutically usual excipients, where the ingredients are in the form of a micronized powder, e.g. having an average particle size of from 10 to 100 µm, by rotagglomeration, extrusion or granulation.

EXAMPLES

Production of Pellets Comprising Mucoadhesively Formulated Peptide and Protein Active Substances Example 1

First Coating (Prepellets):

20 g of Na carboxymethylcellulose (Blanose 7LF, Hercules-Aualon)=10% based on the pellets (water uptake of Blanose 7LF: about 50% in 15 min at pH 7.2 in phosphate buffer, mucoadhesiveness at pH 7.2 in measured by the method of Hassan & Gallo: $\eta_b$=about 250 mPa·s) are dissolved together with 1.25 g of Aerosil 200 (microcrystalline cellulose)=6.25% based on Blanose in 378.8 g of demineralized water by stirring with a propeller stirrer. 0.72 g of polysorbate 80 (33% strength)=40% based on glycerol monostearate (GMS) are dissolved by stirring in 10 g of water. Addition of 0.6 g of GMS=3% based on Blanose and demineralized water ad 20 g is followed by heating of the dispersion to 80° C. The dispersion is cooled to 30° C. and then homogenized with an Ultraturrax mixer for 10 min and subsequently added to the Blanose solution with stirring. Subsequently, 139.4 mg of desmopressin acetate ($M_w$=1067) =0.062% in the formulation are dissolved in 30 g of demin. water and added to the Blanose solution.

200 g of nonpareil pellets 850-1000 μm are introduced into a minifluidized bed apparatus (MiniGlatt from Glatt, Binzen) and coated with the desmopressin-Blanose solution.

Spraying parameters:
Spraying nozzle 0.5 mm
Spraying rate 1-1.26 g/min
Spraying pressure 0.8 bar
Inlet air pressure 1 bar
Inlet air temperature 45° C.
Product temperature 41.5-43° C.
After-drying in the MiniGlatt 10 min at 40° C.
Spraying time: about 2 to 6 h
Drying overnight at RT
Layer thickness (REM): 12-18 μm

TABLE 1

Release (USP XXV method) of desmopressin in phosphate buffer of pH 7.2; 100 min$^{-1}$; paddle; 1 h; 100 rpm; 37° C.; n = 4; (first layer). The released desmopressin is detected using a spectrometer 220 nm.

| | Time [min] | | | | | | | | |
|---|---|---|---|---|---|---|---|---|---|
| | 0 | 5 | 10 | 15 | 20 | 25 | 30 | 45 | 60 |
| Sample 1 [%] | 0.0 | 54.9 | 74.7 | 79.4 | 83.8 | 87.8 | 94.4 | 100.3 | 103.8 |
| Sample 2 [%] | 0.0 | 46.8 | 58.4 | 76.3 | 79.5 | 82.0 | 88.0 | 97.3 | 94.3 |
| Sample 3 [%] | 0.0 | 53.6 | 65.0 | 77.9 | 81.7 | 89.6 | 91.6 | 92.4 | 97.4 |
| Sample 4 [%] | 0.0 | 55.6 | 72.5 | 80.2 | 86.9 | 90.4 | 96.3 | 94.7 | 100.3 |
| Average [%] | 0.0 | 52.7 | 67.7 | 78.4 | 83.0 | 87.4 | 92.6 | 96.2 | 99.0 |
| S.d. [%] | 0.0 | 4.0 | 7.5 | 1.7 | 3.2 | 3.8 | 3.6 | 3.4 | 4.0 |

Example 2

Second Coating (Pellets):

66.7 g of Eudragit® FS30D (30% strength dispersion comprising a copolymer of 25% by weight methyl methacrylate, 65% by weight methyl acrylate and 10% by weight methacrylic acid, Röhm GmbH & Co. KG, Darmstadt) are mixed with 1 g of triethyl citrate (TEC)=5% based on CDM (coating dry matter) in a 150 ml glass beaker. 2.2 g of polysorbate 80 (33% strength)=40% based on GMS are dissolved by stirring in 46 g of demineralized water. Addition of 1.8 g of GMS=9% based on CDM and demineralized water is followed by heating of the dispersion to 80° C. The dispersion is cooled to 30° C. and then homogenized with an Ultraturrax for 10 min and subsequently added with stirring to the Eudragit® FS30D dispersion. After stirring for 30 min, 100 g of the desmopressin-Blanose-coated pellets from Example 2 are therewith introduced into a MiniGlatt and coated with the Eudragit® FS30D dispersion.

Spraying parameters:
Spraying nozzle 0.5 mm
Spraying rate 0.6-0.9 g/min
Spraying pressure 0.7 bar
Inlet air pressure 0.7 bar
Inlet air temperature 30° C.
Product temperature 29-30° C.
After-drying in the MiniGlatt 10 min at 40° C.
Drying overnight at RT
Spraying time: about 1 to 2.5 h
Layer thickness (REM): 40-45 μm

TABLE 2

Desmopressin release from Eudragit ® FS30D coated pellets, 2 h in 0.1 M HCl, 1 h in phosphate buffer of pH 7.2; 100 rpm; paddle; 37° C.; n = 4 (second coating)

| | Time [min] | | | | | | | | |
|---|---|---|---|---|---|---|---|---|---|
| | 0 | 60 | 120 | 125 | 130 | 140 | 145 | 160 | 170 | 180 |
| Sample 1 | 0.0 | 0.0 | 0.0 | 0.0 | 0.0 | 62.7 | 75.1 | 91.3 | 93.4 | 94.1 |
| Sample 2 | 0.0 | 0.0 | 0.0 | 0.0 | 0.0 | 57.1 | 71.0 | 91.4 | 93.2 | 97.1 |
| Sample 3 | 0.0 | 0.0 | 0.0 | 0.0 | 0.0 | 47.0 | 65.4 | 88.5 | 93.4 | 97.5 |
| Sample 4 | 0.0 | 0.0 | 0.0 | 0.0 | 0.0 | 58.8 | 82.4 | 91.7 | 93.7 | 99.2 |
| Average | 0.0 | 0.0 | 0.0 | 0.0 | 0.0 | 56.4 | 73.5 | 90.7 | 93.4 | 97.0 |
| S.d. | 0.0 | 0.0 | 0.0 | 0.0 | 0.0 | 6.7 | 7.2 | 1.5 | 0.2 | 2.1 |

Example 3

First Coating (Prepellets)

20 g of Blanose 7LF=20% based on the pellets (water uptake: about 50% in 15 min at pH 6.0 in phosphate buffer, mucoadhesiveness at pH 6.0 in phosphate buffer measured by the method of Hassan & Gallo: $\eta_b$=about 270 mPa·s) are dissolved together with 1.1 g of Aerosil 200=5.5% based on Blanose and 1.52 g of polysorbate 80 (33% strength) 2.5% based on Blanose in 727.4 g of demineralized water by stirring with a propeller stirrer. 139.4 mg of desmopressin acetate=0.062% in the formulation are then dissolved in 50 g of demineralized water and added to the Blanose solution with stirring.

200 g of neutral cores (non pareilles) 850-1000 μm are introduced into a mini fluidized bed apparatus (Mini-Glatt, Glatt, Binzen) and coated with the desmopressin-Blanose solution.

Spraying parameters:
Spraying nozzle 0.5 mm
Spraying rate 1.4-2.0 g/min
Spraying pressure 1 bar
Inlet air pressure 1.2 bar
Inlet air temperature 45-47° C.
Product temperature 41-42° C.
Spraying time: about 2 to 6 h
After-drying in the MiniGlatt 10 min at 44° C.
Drying overnight at RT
Layer thickness (REM): 10-12 μm

Example 4

Second Coating (Pellets):

66.7 g of (meth)acrylate copolymer dispersion (30 strength dispersion comprising a copolymer of methyl acrylate/butyl methacrylate/ethyl acrylate/methacrylic acid in the ratio 20/20/30/30, Röhm GmbH & Co. KG, Darmstadt) are introduced into a 250 ml glass beaker. 2.4 g of polysorbate 80 (33% strength)=40% based on GMS are dissolved by stirring in 81 g of demineralized water. Addition of 2.0 g of GMS=10% based on the coating dry matter is followed by heating of the dispersion to 80° C. The dispersion is cooled to 30° C. and then homogenized with an Ultraturrax for 10 min and subsequently added with stirring to the product 4154 D dispersion. After stirring for 30 min, 100 g of the desmopressin-Blanose-coated pellets from Example 3 are introduced therewith into a MiniGlatt and coated with the dispersion.

Spraying parameters:
Spraying nozzle 0.5 mm
Spraying rate 0.6-0.9 g/min
Spraying pressure 0.5 bar
Inlet air pressure 0.7 bar
Inlet air temperature 35-37° C.
Product temperature 32-33° C.
After-drying in the MiniGlatt 10 min at 40° C.
Spraying time: about 1 to 2 h
Drying overnight at RT
Layer thickness (REM): 40-45 μm

TABLE 4

Desmopressin release of the pellets coated with the abovementioned copolymer, 2 h in 0.1 M HCl, 1 h in phosphate buffer of pH 6.0; 100 rpm; paddle; 37° C.; n = 4 (second coating)

| | Time [min] | | | | | | | | | |
|---|---|---|---|---|---|---|---|---|---|---|
| | 0 | 60 | 120 | 125 | 130 | 140 | 145 | 160 | 170 | 180 |
| Sample 1 | 0.0 | 0.0 | 0.0 | 0.0 | 0.0 | 24.8 | 47.4 | 93.0 | 98.0 | 102.4 |
| Sample 2 | 0.0 | 0.0 | 0.0 | 0.0 | 0.0 | 22.4 | 40.7 | 87.2 | 92.5 | 98.2 |
| Sample 3 | 0.0 | 0.0 | 0.0 | 0.0 | 0.0 | 20.8 | 42.5 | 88.4 | 95.6 | 101.5 |
| Sample 4 | 0.0 | 0.0 | 0.0 | 0.0 | 0.0 | 25.1 | 41.9 | 88.9 | 98.8 | 97.9 |
| Average | 0.0 | 0.0 | 0.0 | 0.0 | 0.0 | 23.3 | 43.1 | 89.3 | 96.2 | 100.0 |
| S.d. | 0.0 | 0.0 | 0.0 | 0.0 | 0.0 | 2.0 | 2.9 | 2.5 | 2.8 | 2.3 |

Example 5

First Coating (Pre-Pellets):

15 g of chitosan low MW (Fluka)=10% based on the pellets (water uptake of chitosan: about 140% in 15 min at pH 5.5 in acetate buffer, mucoadhesiveness at pH 5.5 measured by the method of Hassan & Gallo: eta-b=about 220 mPa·s) are dispersed together with 0.825 g of Aerosil 200=5.5% based on chitosan in 1122 g of demineralized water and 1.36 g of polysorbate 80 (33% strength)=3% based on chitosan by stirring with a propeller stirrer. The chitosan is then dissolved by adding 60 g of acetic acid while continuing the stirring for 1 h. 104.6 mg of desmopressin acetate=0.063% in the formulation dissolved in 50 g of demin. water and added to the chitosan solution.

150 g of non pareil pellets 850-1000 μm are introduced into a MiniGlatt (Glatt, Binzen) and coated with the desmopressin-chitosan solution.

Spraying parameters:
Spraying nozzle 0.5 mm
Spraying rate 0.8-2.5 g/min
Spraying pressure 1.5-1.8 bar
Inlet air pressure 1.1-1.2 bar
Inlet air temperature 60-69° C.
Product temperature 59-62° C.
After-drying in the MiniGlatt 10 min at 50° C.
Spraying time 3-8 h
Drying overnight at RT
Layer thickness (REM): 12 μm

TABLE 5

Release of desmopressin in phosphate buffer of pH 5.5; 100 min$^{-1}$; paddle; 1 h; 100 rpm; 37° C.; n = 4 (first layer)

| | Time [min] | | | | | | | |
|---|---|---|---|---|---|---|---|---|
| | 0 | 5 | 10 | 15 | 20 | 25 | 30 | 45 | 60 |
| Sample 1 | 0.0 | 71.9 | 89.4 | 98.3 | 94.5 | 93.4 | 91.7 | 91.8 | 96.2 |
| Sample 2 | 0.0 | 68.6 | 91.5 | 105.3 | 99.3 | 92.9 | 100.3 | 104.0 | 98.6 |
| Sample 3 | 0.0 | 76.7 | 91.1 | 100.1 | 98.1 | 101.1 | 101.6 | 101.2 | 102.5 |

TABLE 5-continued

Release of desmopressin in phosphate buffer of pH 5.5; 100 min$^{-1}$;
paddle; 1 h; 100 rpm; 37° C.; n = 4 (first layer)

| | Time [min] | | | | | | | | |
|---|---|---|---|---|---|---|---|---|---|
| | 0 | 5 | 10 | 15 | 20 | 25 | 30 | 45 | 60 |
| Sample 4 | 0.0 | 70.7 | 92.6 | 100.3 | 94.8 | 99.5 | 99.3 | 97.1 | 94.6 |
| Average | 0.0 | 72.0 | 91.1 | 101.0 | 96.7 | 96.7 | 98.2 | 98.5 | 98.0 |
| S.d. | 0.0 | 3.4 | 1.4 | 3.0 | 2.4 | 4.2 | 4.4 | 5.3 | 3.4 |

Example 6

Second Coating (Pellets):

66.7 g of Eudragit® L30D-55 (30% strength dispersion comprising a (meth)acrylate copolymer composed of 50% by weight methacrylic acid and 50% by weight ethyl acrylate) are mixed with 2 g of triethyl citrate (TEC)=10% based on CDM (coating dry matter) in a 150 ml glass beaker. 0.73 g of polysorbate 80 (33% strength)=40% based on GMS are dissolved by stirring in 46 g of demineralized water. Addition of 0.6 g of GMS=3% based on CDM and demineralized water is followed by heating of the dispersion to 80° C. The dispersion is cooled to 30° C. and then homogenized with an Ultraturrax for 10 min and subsequently added with stirring to the Eudragit® L30D-55 dispersion. After stirring for 30 min, 100 g of the desmopressin-chitosan-coated pellets from Example 5 are introduced therewith into a MiniGlatt and coated with the Eudragit® L30D-55 dispersion.

Example 7

Sprayability

TABLE 7

Survey of the sprayability (yes/no) of the polymer
dispersions/or solutions at various concentrations.

| | Concentration | | |
|---|---|---|---|
| Mucoadhesive polymer | 1.25% | 2% | 5% |
| pH 5.5 | | | |
| Blanose 7LF (Na-CMC) | n.a. | yes | yes |
| Chitosan (low Mw) | yes | no | no |
| Methocel A15 (methylcellulose) | n.a. | yes | yes |
| pH 7.2 | | | |
| (Meth)acrylate copolymer* | n.a. | yes | yes |
| Methocel A15 (methylcellulose) | n.a. | yes | yes |
| Blanose 7LF (Na-CMC)* | n.a. | yes | yes |

*(Meth)acrylate copolymer of 30% by weight methyl methacrylate and 70% by weight methacrylic acid Example 8

Formulation Examples for Targeted Release of Active Substance in Various Sections of the Intestine (see Table 8)

Particle size after coating, finished formulation on use of non pareil pellets 850-1000 as carrier material μm→900-1050 μm

TABLE 8

Formulations and polymer properties

| pH in relevant section of intestine | Formulation composition in the formulation | Percentage | Properties of mucoadhesive polymer | Active substance * in mucoadh. polymer ** in the form. | Further excipients | Indication, therapy |
|---|---|---|---|---|---|---|
| 5.5 | 1$^{st}$ Layer: | | Chitosan | * Desmopressin, 0.70% | | Diabetes insipidus |
| Duodenum | Neutral pellets 0.85-1 mm | 72.2% | (Na-CMC) | ** Desmopressin, 0.050% | | |
| | Chitosan | 7.2% | $\eta_b$ = *** = ca. | | | |
| | Acetic acid for dissolving | | 220 mPa · s | | | |
| | Aerosil 200 | 0.4% | Water uptake = ca. | | | |
| | Polysorbate 80 | 0.22% | 140% in 15 min | | | |
| | 2$^{nd}$ Layer: | | | | | |
| | Eudragit ® L30D-55 | 16.0% | | | | |
| | TEC | 1.6% | | | | |
| | GMS | 1.6% | | | | |
| | Polysorbate 80 | 0.64% | | | | |
| 6.0 | 1$^{st}$ Layer: | | Blanose 7LF | * Insulin, 4.75% | **Polyethylene 660 | Diabetes |
| Jejunum | Neutral pellets 0.85-1 mm | 73.2% | (Na-CMC) | ** Insulin, 0.35% | 12-hydroxystearate | mellitus |
| | Blanose 7LF | 7.3% | Eta b * = ca. | | (Solutol ® HS15) | (basic |
| | Aerosil 200 | 0.4% | 270 mPa · s | | up to 2% | therapy) |
| | Polysorbate 80 | 0.18% | Water uptake = ca. | | | |
| | 2$^{nd}$ Layer: | | 50% in 15 min | | **Na Glycocholate | |
| | Copolymer of Example 4 | 16.3% | | | up to 1% | |
| | GMS | 1.6% | | | **Aprotinin up | |
| | Polysorbate 80 | 0.65% | | | to 1% | |

TABLE 8-continued

Formulations and polymer properties

| pH in relevant section of intestine | Formulation composition in the formulation | Percentage in the formulation | Properties of mucoadhesive polymer | Active substance * in mucoadh. polymer ** in the form. | Further excipients | Indication, therapy |
|---|---|---|---|---|---|---|
| 6.0 Jejunum | 1st Layer: Neutral pellets 0.85-1 mm Blanose 7LF Aerosil 200 Polysorbate 80 2nd Layer: Copolymer of Example 4 GMS Polysorbate 80 | 71.9% 7.2% 0.4% 0.18% 16.3% 1.6% 0.65% | Blanose 7LF (Na-CMC) Eta b * = ca. 270 mPa · s Water uptake = ca. 50% in 15 min | * Cetrorelix, 24% ** Cetrorelix, 1.73% and other LHRH antagonists | Polyoxyethylene- polyoxypropylene glycol (Pluronic ® F68) up to 2% | Carcinoma of breast Carcinoma of prostate |
| 7.2 Ileum Descending colon | 1st Layer: Neutral pellets 0.85-1 mm Blanose 7LF Aerosil 200 GMS Polysorbate 80 2nd Layer: Eudragit ® FS30D TEC GMS Polysorbate 80 | 72.8% 7.3% 0.46% 0.22% 0.087% 16.2% 0.81% 1.46% 0.58% | Blanose 7LF (Na-CMC) Eta b * = ca. 250 mPa · s Water uptake = ca. 52% in 15 min | * Desmopressin, 0.95% ** Desmopressin, 0.069% | | Enuresis nocturna |
| 7.2 Ileum Descending colon | 1st Layer: Neutral pellets 0.85-1 mm Blanose 7LF Aerosil 200 GMS Polysorbate 80 2nd Layer: Eudragit ® FS30D TEC GMS Polysorbate 80 | 63.5% 12.7% 0.79% 0.38% 0.152% 16.2% 0.81% 1.46% 0.58% | Blanose 7LF (Na-CMC) Eta b* = ca. 250 mPa · s Water uptake = ca. 52% in 15 min | * Ciclosporin A, 27.2% ** Ciclosporin A, 3.45% | **Polyethylene 660 12-hydroxystearate (Solutol ® HS15) up to 2% | Immuno- suppressant |

*** Measurement of the mucoadhesive property by the method of Hassan and Gallo

Examples of Embodiments Having an Active Substance-Containing Lipophilic Matrix

1st Example

Embodiment of a Formulation for a Slightly Soluble Proteins (Erythropoetin alfa; solubility in water according to DAB 10 at least 500 parts of water for 1 part of active substance; equivalent to 2 g/l).

a) Preparation of the Lipophilic Phase.

100 g of Inwitor 312 (melting point 55-60° C.) are melted in a waterbath at 65° C., and 50 g of Inwitor 308 (melting point 30-34° C.) are slowly stirred into the melt. The waterbath is cooled down to 50° C., and 7.5 g of tocopherol acetate, 2 and 3.5 g of Na glycocholate are added while stirring. The temperature of the bath can thus be reduced by a further 5° C. without the fat resolidifying. The resulting lipophilic matrix thus has a melting point of 38-41° C. and a solubility in water, calculated from the individual components, according to DAB 10 of at least 400 parts of water for 1 part of lipophilic matrix; equivalent to 2.5 g/l). 330 mg of erythropoetin alfa (about 40 million I.U.) are added to this solution while stirring.

b) Preparation of an Emulsion 750 ml of distilled water are initially heated at 45° C., and 15 g of Na caprate as emulsifier (2%) are added. This solution is then adjusted to a pH of about 7 by adding citric acid. Thereafter, 1.5 g of soybean trypsin inhibitor (serine peptidase inhibitor) and 1.5 g of bacitracin (aminopeptidase inhibitor) are added to this solution while stirring. The lipophilic phase is then emulsified in this solution by vigorous stirring. The emulsion process can be terminated when no lipophilic droplets larger than 50-60 µm are evident after microscopic investigation.

c) Production of Mucoadhesive Cores 350 g of Na alginate powder, 145 of microcrystalline cellulose and 5 g of citric acid are mixed thereto in a GPCG1 with rotor insert. The emulsion described in b) is sprayed as binder in the rotoagglomeration process at a spraying rate of about 90 g/min.

The rotor is set at 1700-1800 rpm, the inlet air at 42 m³/hour and the temperature of the air at 30° C.

Under these conditions it is possible to produce mucoadhesive cores between 250 and 600 µm with a yield of up to 80%.

A therapeutic dosage of 240 µg is present in 0.5 g of pellet cores.

d) Production of Coated Pellets

The pellet cores from c) are coated with Eudragit® FS30D by means of a conventional fluidized bed processes. The application of polymer amounts to 40% by weight based on the core weight. The dispersion/suspension for coating consists of:

| | |
|---|---|
| Eudragit ® FS30D | 44.65% |
| Triethyl citrate | 0.67% |
| Polysorbate 80 | 0.26% |
| Glycerol monostearate | 0.67% |
| Water | 53.75% |

The pellets obtained in this way can be compressed to a tablet using conventional pharmaceutical processes and excipients or packed into capsules.

2$^{nd}$ Example

Embodiment of a Formulation for Slightly Soluble Peptides (Cetrorelix acetate; solubility in water according to DAB 10 at least 1000 parts of water for 1 part of active substance; equivalent to 1 g/l).
a) Preparation of the Lipophilic Phase
13 g of Imwitor 312 (melting point 55-60° C.) are melted with 4 g of Poloxamer 407 (Lutrol F127, melting point 50-55° C.) in a waterbath at 65° C. Then 1 g of caprylic acid, 1 g of Na caprylate and 1 g of tocopherol acetate are added while stirring. The resulting lipophilic matrix thus has a melting point of 40-48° C. and a solubility in water, calculated from the individual components, according to DAB 10 of at least 700 parts of water for 1 part of lipophilic matrix (equivalent to 1.5 g/l). After the solution has been cooled to 45° C., 3.0 g of cetrorelix acetate are stirred into the lipophilic phase while stirring at high speed, and cooled.
b) Production of an Emulsion
The resulting dispersion from a) is dispersed using an Ultraturrax (20 000 rpm) with the chitosan citrate dispersion from b) while cooling further in an ice bath to 10° C. for a min. of 10 min. The emulsification process can be terminated when no lipophilic droplets larger than 50-60 μm are evident after microscopic examination.
c) Production of Mucoadhesive Cores
20 g of chitosan are dispersed in 1000 g of water and then, while stirring at very high speed, 20 g of citric acid. 2 g of Na dodecanate are added to the resulting clear yellowish viscous solution while stirring at high speed, and stirring is continued for 1 h.
The emulsion from b) is sprayed using a GPCG1 (Glatt) at a spraying rate of 10-12 g/min/kg onto 250 g of neutral pellets 400-600 μm at an inlet air temperature of 30° C. and. The inlet air is in this case set at 45-50 m$^3$/h.
The yield in this case is 90%.
d) Production of Coated Pellets
The pellets obtained in this way are coated with Eudragit® L12.5 by means of conventional fluidized bed processes. The application of polymer amounts to 40% by weight based on the core weight. The suspension for coating consists of:

| | |
|---|---|
| Eudragit ® L12.5 | 53.3% |
| Triethyl citrate | 1.33% |
| Isopropanol | 38.3% |
| Talc | 2.0% |
| Water | 5.0% |

The pellets obtained in this way can be compressed to a tablet using conventional pharmaceutical processes and excipients, or packed into capsules.

3$^{rd}$ Example

Embodiment of a Formulation for a Slightly Soluble Protein (beta-Interferon human; solubility in water according to DAB 10 at least 600 parts of water for 1 part of active substance; equivalent to 2 g/l)
a) Preparation of the Lipophilic Phase
400 g of Imwitor 312 (melting point 55-60° C.) and 200 g of Dynasan 114 (melting point 55-58° C.) are melted with 30 g of tocopherol acetate at 65° C. and put into a granulator (Bohle). 20 g of Na caprylate are added thereto with stirring. The mixture is cooled to 45° C. and 100 g of interferon-beta are dissolved therein. The resulting lipophilic matrix thus has a melting point of 39-46° C. and a solubility in water, calculated from the individual components, according to DAB 10 of at least 840 parts of water for 1 part of lipophilic matrix. The lipophilic matrix is ground while cooling to a particle size below 50 μm.
b) Production of a Buffer Solution
1 g of Na citrate and 1 g of citric acid are dissolved in 500 g of water. While stirring at high speed, 0.5 g of Na cholate and 100 mg of soybean trypsin inhibitor are added.
c) Granulation
The ground active substance-containing lipophilic matrix from a) is mixed in a granulator with 1500 g of Blanose 7LF. The aqueous buffer solution from b) is then used for granulation to result in particles 0.2 to 0.5 mm in size, which are rounded on a Spheronizer. The resulting moist cores are dried under mild conditions at 30 to 25° C. in a fluidized bed dryer.
d) Production of Coated Pellets
The thus cores from c) are coated with Eudragit® FS30D using conventional fluidized bed processes. The application of polymer amounts to 40% by weight based on the core weight. The dispersion/suspension for coating consists of:

| | |
|---|---|
| Eudragit ® FS30D | 44.65% |
| Triethyl citrate | 0.67% |
| Polysorbate 80 | 0.26% |
| Glycerol monostearate | 0.67% |
| Water | 53.75% |

The pellets obtained in this way can be compressed to tablets using conventional pharmaceutical processes and excipients, or packed into capsules.

The invention claimed is:
1. An oral multiparticulate pharmaceutical form comprising pellets having a size in the range from 50 to 2,500 which comprise:
    a) a mucoadhesive inner matrix layer consisting essentially of a mucoadhesive polymer having a mucoadhesive effect and an active substance which is a peptide or a protein, which may include non-natural amino acid residue(s), embedded in the mucoadhesive polymer, and
    b) an outer film coating consisting essentially of an anionic polymer or copolymer,
    wherein the mucoadhesive inner matrix layer does not contain gelatin, wherein said multiparticulate pharmaceutical form is formulated so that the contained pellets are released in the pH range of the stomach, wherein the outer coatings of the pellets are adjusted through the choice of the anionic polymer or copolymer or its formulation with excipients and its layer thickness such that the coating dissolves in pH ranges from 4.0 to 8.0 in the intestine within 15 to 60 min, so that the active substance-containing, mucoadhesive inner matrix layer is exposed and binds to the intestinal mucosa, protects the active substance from physical, chemical, and enzymatic inactivation and releases the active substance there, wherein the active substance content embedded in the mucoadhesive polymer of the mucoadhesive inner matrix layer is a maximum of 40% by weight based on the weight of the mucoadhesive polymer having a mucoadhesive effect, and wherein the mucoadhesive polymer having a mucoadhesive effect exhibits a mucoadhesive effect of $\eta_b=150$ to 1000 mPa·s and a water uptake of from 10 to 750% in 15 min in a range of +/−0.5 pH units relative to the pH at which the outer coating starts to dissolve and is selected from the group consisting of at least one of chitosan, a (meth)acrylate copolymer consisting of 20-40% by weight methyl methacrylate and 60 to 80% by weight methacrylic acid, a crosslinked polyacrylic acid, an uncrosslinked polyacrylic acid, an Na alginate, and a pectin.

2. The oral multiparticulate pharmaceutical form of claim 1, wherein the outer film coating consists of a (meth)acrylate copolymer having a content of monomers having anionic groups of from 5 to 60% by weight.

3. The oral multiparticulate pharmaceutical form of claim 1, wherein the layer thickness of the outer coating is in the range from 20 to 200 μm.

4. The oral multiparticulate pharmaceutical form of claim 1, wherein the mucoadhesive polymer in the mucoadhesive inner matrix is chitosan; the active pharmaceutical ingredient is Cetrorelix; and the outer coating is a copolymer of 50 wt % methylmethacrylate and 50 wt % methacrylic acid.

5. The oral multiparticulate pharmaceutical form of claim 4, wherein the mucoadhesive inner matrix contains as polymer having a mucoadhesive effect a chitosan which is employed together with an acid or a buffer system, which is located in the matrix or in or on a core onto which the matrix is applied.

6. The oral multiparticulate pharmaceutical form of claim 5, wherein the mucoadhesive inner matrix layer contains chitosan and is adjusted to pH 5.0 to 5.5 by means of an acid or a buffer system, and is combined with an outer film coating which starts to dissolve in the range from pH 6.0 to 8.0.

7. The oral multiparticulate pharmaceutical form of claim 1, wherein the active substance is a protein or a peptide having an average molecular weight $M_w$ of less than 3,000 Da.

8. The oral multiparticulate pharmaceutical form of claim 7, wherein the active substance is selected from the group consisting of abarelix angiogenesis II, anidulafungin, antide, argipressin, azaline and azaline B, bombesin antagonist, bradykinin, buserelin, cetrorelix, cyclosporin A, desmopressin, detirelix, encephalins (Leu-, Met-) ganirelix, gonadorelin, goserelin, growth hormone secretagogue, micafungin, nafarelin, leuprolide, leuprorelin, octreotide, orntide, oxytocin, ramorelix, secretin, somatotropin, terlipressin, tetracosactide, teverelix, triptorelin, thyroliberin, thyrotropin, vasopressin and mixtures thereof.

9. The oral multiparticulate pharmaceutical form of claim 7, wherein the mucoadhesive inner matrix layer additionally contains a $C_6$- to $C_{20}$-fatty acid and/or a $C_6$- to $C_{20}$-alcohol including their salts, ether, ester or amide derivatives and/or a lipid and/or a phospholipid and/or a lipid-soluble vitamin.

10. A composition containing pellets ranging in size from 50 to 2,500 μm that comprise:

a mucoadhesive inner matrix layer consisting essentially of 40 wt. % or less of an active pharmaceutical ingredient embedded in a mucoadhesive polymer having a mucoadhesive effect of at least $\eta_B$ of 150 to 1,000 mPa·s and a water uptake ranging from 10 to 750% in 15 min at a pH between 5.5 and 7.2, and an outer coating of anionic polymer or anionic copolymer;

wherein the mucoadhesive inner matrix layer does not contain gelatin;

wherein said pellets do not have a layer separating the mucoadhesive inner matrix and outer coating; and wherein the outer coating dissolves at a pH ranging from 5.5 to 7.2 within 15 to 60 mins.

11. The composition of claim 10, wherein the mucoadhesive inner matrix consists essentially of chitosan and Cetrorelix; and the outer coating is a copolymer of 50 wt % methylmethacrylate and 50 wt % methacrylic acid.

12. The oral multiparticulate pharmaceutical form comprising pellets having a size in the range from 50 to 2,500 μm, which comprise:

a) a mucoadhesive inner matrix layer consisting essentially of:
  (1) a mucoadhesive polymer having a mucoadhesive effect,
  (2) a substance selected from the group consisting of a $C_6$- to $C_{20}$-fatty acid, the salts, ether, ester and amide derivatives of a $C_6$- to $C_{20}$-fatty acid, the salts, ether, ester and amide derivatives thereof, a $C_6$- to $C_{20}$-alcohol, the ether, ester and amide derivatives thereof, a lipid, a phospholipid, a lipid-soluble vitamin, and mixtures thereof, and
  (3) an active peptide or a protein, which may include non-natural amino acid residue(s), embedded in the mucoadhesive polymer; and b) an outer film coating consisting essentially of an anionic polymer or copolymer, wherein the mucoadhesive inner matrix layer does not contain gelatin, wherein said multiparticulate pharmaceutical form is formulated so that the contained pellets are released in the pH range of the stomach, wherein the outer coatings of the pellets are adjusted through the choice of the anionic polymer or copolymer or its formulation with excipients and its layer thickness such that the coating dissolves in pH ranges from 4.0 to 8.0 in the intestine within 15 to 60 min, so that the active substance-containing, mucoadhesive inner matrix layer is exposed and binds to the intestinal mucosa, protects the active substance from physical, chemical, and enzymatic inactivation and releases the active substance there, wherein the active substance content embedded in the mucoadhesive polymer of the mucoadhesive inner matrix layer is a maximum of 40% by weight based on the weight of the mucoadhesive polymer having a mucoadhesive effect, and wherein the mucoadhesive polymer having a mucoadhesive effect exhibits a mucoadhesive effect of $\eta_b=150$ to 1000 mPa·s and a water uptake of from 10 to 750% in 15 min in a range of +/−0.5 pH units relative to the pH at which the outer coating starts to dissolve and is selected from the group consisting of at least one of chitosan, a (meth)acrylate copolymer consisting of 20-40% by weight methyl methacrylate and 60 to 80% by weight methacrylic acid, a crosslinked polyacrylic acid, an uncrosslinked polyacrylic acid, an Na alginate, and a pectin.

13. The oral multiparticulate pharmaceutical form of claim 12, wherein the mucoadhesive inner matrix layer contains a substance selected from the group consisting of $C_6$- to $C_{20}$-fatty acids, and a salt, ether, ester and amide thereof; $C_6$- to $C_{20}$-alcohols, and an ether, ester and amide thereof; and mixtures thereof.

14. The oral multiparticulate pharmaceutical form of claim 12, wherein the mucoadhesive inner matrix layer contains a substance selected from the group consisting of a lipid, a phospholipid, a lipid-soluble vitamin, and mixtures thereof.

15. The oral multiparticulate pharmaceutical form of claim 1, wherein the content of the active substance in the mucoadhesive inner matrix layer is 0.001 to 15% by weight of the content of the mucoadhesive polymer having a mucoadhesive effect.

16. The composition of claim 10, wherein the content of the active substance in the mucoadhesive inner matrix layer is 0.001 to 15% by weight of the content of the mucoadhesive polymer having a mucoadhesive effect.

17. The oral multiparticulate pharmaceutical form of claim 12, wherein the content of the active substance in the mucoadhesive inner matrix layer is 0.001 to 15% by weight of the content of the mucoadhesive polymer having a mucoadhesive effect.

18. The oral multiparticulate pharmaceutical form of claim 1, wherein the content of the active substance in the mucoadhesive inner matrix layer is 0.05 to 5% by weight of the content of the mucoadhesive polymer having a mucoadhesive effect.

19. The composition of claim 10, wherein the content of the active substance in the mucoadhesive inner matrix layer is 0.05 to 5% by weight of the content of the mucoadhesive polymer having a mucoadhesive effect.

20. The oral multiparticulate pharmaceutical form of claim 12, wherein the content of the active substance in the mucoadhesive inner matrix layer is 0.05 to 5% by weight of the content of the mucoadhesive polymer having a mucoadhesive effect.

* * * * *